United States Patent
Yasunaga et al.

(10) Patent No.: US 9,500,851 B2
(45) Date of Patent: Nov. 22, 2016

(54) ENDOSCOPE

(71) Applicant: OLYMPUS CORPORATION, Tokyo (JP)

(72) Inventors: Koji Yasunaga, Hino (JP); Yuta Sekiguchi, Hachioji (JP); Yuta Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/132,468

(22) Filed: Apr. 19, 2016

(65) Prior Publication Data

US 2016/0231556 A1   Aug. 11, 2016

Related U.S. Application Data

(63) Continuation of application No. PCT/JP2015/055421, filed on Feb. 25, 2015.

(30) Foreign Application Priority Data

Apr. 11, 2014  (JP) ................... 2014-082269

(51) Int. Cl.
  *G01D 21/00* (2006.01)
  *G02B 23/24* (2006.01)
  *G01D 11/16* (2006.01)
  *A61B 1/005* (2006.01)
  *F16L 55/40* (2006.01)
  *A61B 1/00* (2006.01)

(52) U.S. Cl.
  CPC ......... *G02B 23/2476* (2013.01); *A61B 1/0057* (2013.01); *G01D 11/16* (2013.01); *A61B 1/00098* (2013.01); *F16L 55/40* (2013.01)

(58) Field of Classification Search
  CPC . G02B 23/2476; A61B 1/0057; G01D 11/16
  USPC ......................................... 73/866.5; 600/101
  See application file for complete search history.

(56) References Cited

U.S. PATENT DOCUMENTS 5,618,307 A * 4/1997 Donlon ............ A61B 17/00234
                                                          604/158
2008/0275302 A1   11/2008 Hosaka
(Continued)

FOREIGN PATENT DOCUMENTS

| JP | 2004-129785 A | 4/2004 |
| JP | 2004-321492 A | 11/2004 |
| JP | 2008-035882 A | 2/2008 |

(Continued)

OTHER PUBLICATIONS

International Search Report dated May 26, 2015 issued in PCT/JP2015/055421.

*Primary Examiner* — Max Noori
(74) *Attorney, Agent, or Firm* — Scully, Scott, Murphy & Presser, PC

(57) ABSTRACT

An endoscope includes: an insertion portion; an operation portion; a bending wire that causes a bending portion to bend by pulling; a bending operation member that gives pulling force to the bending wire by swinging; an operation force reduction portion including a spring that can press the bending operation member; and a semi-fixation mechanism switch operation member that makes a switch to a pressing state, in which the spring presses the bending operation member, and to a non-pressing state.

10 Claims, 15 Drawing Sheets

(56) References Cited

U.S. PATENT DOCUMENTS

| | | | | |
|---|---|---|---|---|
| 2012/0088963 A1* | 4/2012 | Yasunaga | ............ | A61B 1/00149 600/102 |
| 2013/0012781 A1* | 1/2013 | Kaneko | .............. | A61B 1/00066 600/148 |
| 2013/0338441 A1* | 12/2013 | Okamoto | ............. | A61B 1/0052 600/146 |
| 2016/0192823 A1* | 7/2016 | Yasunaga | ............. | A61B 1/0052 600/109 |

FOREIGN PATENT DOCUMENTS

| | | |
|---|---|---|
| JP | 2010-183949 A | 8/2010 |
| JP | 2012-029822 A | 2/2012 |
| JP | 2013-223735 A | 10/2013 |

\* cited by examiner

ENDOSCOPE

CROSS REFERENCE TO RELATED APPLICATION

This application is a continuation application of PCT/JP2015/055421 filed on Feb. 25, 2015 and claims benefit of Japanese Application No. 2014-082269 filed in Japan on Apr. 11, 2014, the entire contents of which are incorporated herein by this reference.

BACKGROUND OF INVENTION

1. Field of the Invention

The present invention relates to an endoscope that includes a bending portion on a distal end side of an insertion portion and performs bending operation of the bending portion by a bending operation member provided on an operation portion on a hand side.

2. Description of the Related Art

In recent years, endoscopes have been utilized in a medical field and an industrial field. There is an endoscope provided with a bending portion on a distal end side of an elongated insertion portion. In general, a bending operation member provided on an operation portion on a proximal end side of the insertion portion is operated by hand to perform bending motion of the bending portion in a desired direction.

Examples of the bending operation member provided on the operation portion include a bending knob or a bending lever rotated and operated about an axis and a joy stick lever tilted and operated.

The bending portion provided in the insertion portion is covered by bending rubber with elastic force. A plurality of endoscope built-in parts, such as a treatment instrument channel tube, an air feeding tube, a water feeding tube, a signal cable including a bundle of a plurality of signal lines, and an illumination light guide, are inserted and arranged in the insertion portion. The endoscope built-in parts serve as elastic resistances when the bending portion is bent. Therefore, when the bending portion is bent, elastic restoring force (see a solid line L of FIG. 1) for returning the bending portion to a straight line state acts on the bent bending portion due to the bending rubber and the endoscope built-in parts.

Furthermore, when the endoscope is bent, the built-in parts come into contact with each other and generate friction force.

Bending portion resistance force that is a combination of the elastic restoring force and the friction force increases with an increase in a bending angle of the bending portion.

Therefore, when the bending portion is bent, a user operates the bending operation member by bending operation force indicated by a first dashed line L1 of FIG. 1 that is force against the bending portion resistance force. In this case, the bending portion resistance force increases with an increase in the bending angle of the bending portion, and the bending operation force for operating the bending operation member also increases.

As a result, a load on a finger of the user becomes large. When the user temporarily separates the finger from the bending operation member during the operation, the bending angle may be reduced by the elastic restoring force or the like of the bending rubber and the endoscope built-in parts, and the user may lose sight of an observed site.

In order to resolve the trouble, an operation portion of a conventional endoscope is provided with, for example, a semi-fixation mechanism including a lever, a cam mechanism, and a friction plate. The semi-fixation mechanism is a mechanism that makes a switch to a semi-fixation state and a semi-fixation release state, wherein in the semi-fixation state, lever operation brings the friction plate into contact with, for example, a drum to which one end of a bending wire is fixed, and in the semi-fixation release state, the friction plate is separated from the drum.

In the semi-fixation state, the bending portion can perform bending motion along with the operation of the bending operation member. On the other hand, when the user separates the finger from the bending operation member, the bending portion holds a bending state before the separation. Therefore, when the user captures a target observed site, the user selects the semi-fixation state to perform observation and the like while preventing losing sight of the observed site.

Note that the bending operation force for operating the bending operation member varies between first bending operation force indicated by the first dashed line L1, in which the bending angle of the bending portion increases, and bending holding force indicated by a second dashed line 2, in which the bending angle is held in this state, and the bending holding force is smaller than the elastic restoring force.

This is because the bending rubber and the endoscope built-in parts act as restoring force when the bending angle of the bending portion is increasing, and the friction force acts in an opposite direction of the restoring force when the bending angle is held. In other words, to prevent the bending angle of the bending portion from changing when the finger is separated from the bending operation member during the operation of the bending operation member, semi-fixation force (force F with a magnitude indicated by an arrow of FIG. 1) for canceling the bending holding force can be provided from the semi-fixation mechanism to the drum.

SUMMARY OF THE INVENTION

An aspect of the present invention provides an endoscope including: an insertion portion that is inserted to a portion to be observed and is provided with a bending portion bendable in at least two directions relative to an insertion axis direction; an operation portion continuously connected to a proximal end side of the insertion portion; a pulling member with a distal end connected to the bending portion, the pulling member causing the bending portion to bend by pulling; a bending operation member to which a proximal end of the pulling member is connected, the bending operation member being provided to be swingable about a fulcrum provided on the operation portion, the bending operation member giving pulling force to the pulling member by swinging; an operation force reduction portion including a first end portion and a second end portion, the first end portion being connected in a swingable manner to the bending operation member at a connection portion protruding at a predetermined height from the fulcrum, the operation force reduction portion including an elastic member that can press the bending operation member through the first end portion; and a switch operation member that makes a switch to a pressing state, in which the elastic member presses the bending operation member, and to a non-pressing state.

BRIEF DESCRIPTION OF THE DRAWINGS

FIG. 6B is a diagram describing the semi-fixation release state of the semi-fixation mechanism switch operation member;

DETAILED DESCRIPTION OF THE PREFERRED EMBODIMENT(S)

Figure 1:
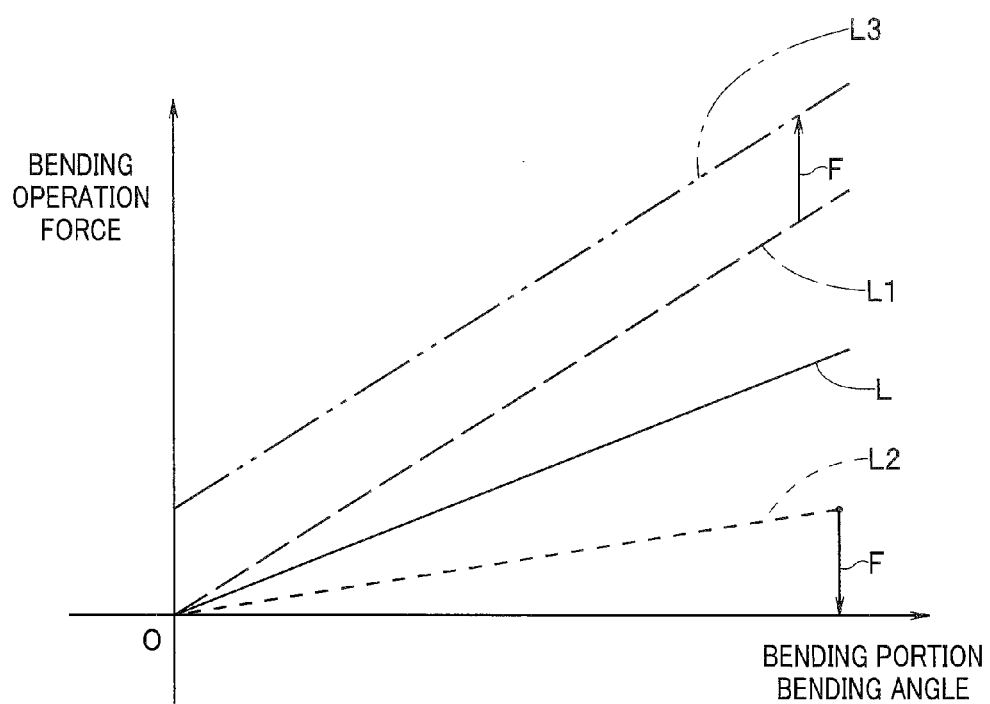
FIG. 1 is a diagram describing a relationship between a bending angle of a bending portion and bending operation force for operating a bending operation member in a conventional endoscope.

Hereinafter, an embodiment of the present invention will be described with reference to the drawings.

Note that, each drawing used in the following description is schematically illustrated, and a dimensional relationship, a scale, and the like of each member may vary in each constituent element in order to illustrate each constituent element in size that allows recognizing the constituent element on the drawing. Therefore, the present invention is not limited only to quantities of the constituent elements described in the drawings, shapes of the constituent elements, ratios of sizes of the constituent elements, relative positional relationship between respective constituent elements, and other illustrated modes.

Figure 2:
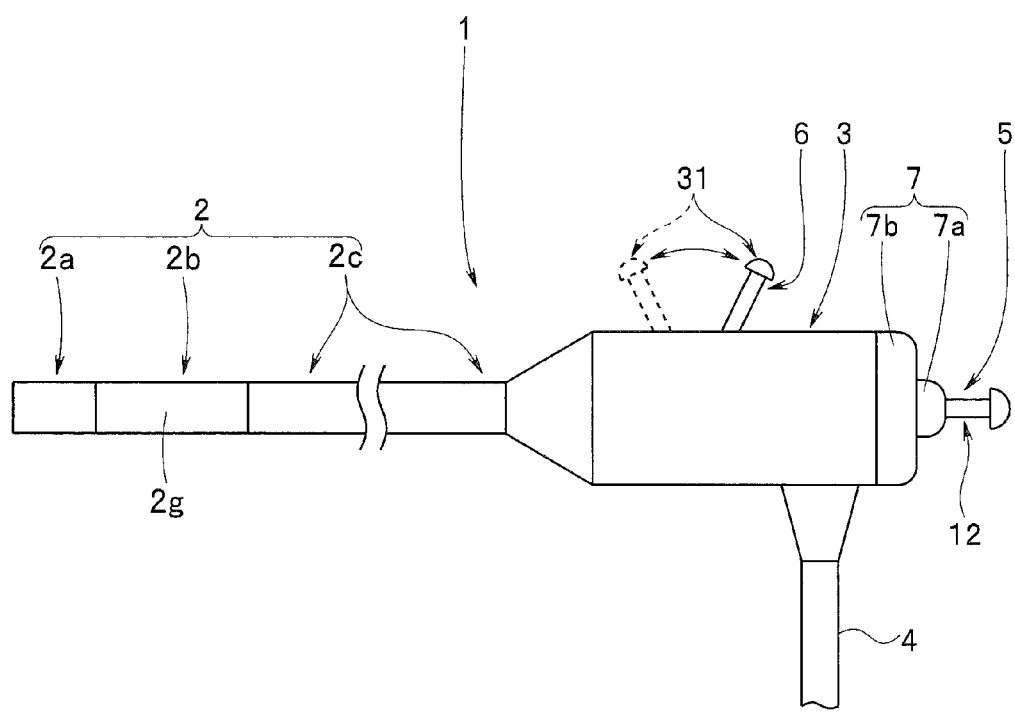
FIG. 2 is a schematic diagram of an endoscope including a bending operation member and a semi-fixation mechanism switch operation member in an operation portion.

As shown in FIG. 2, an endoscope 1 includes: a long insertion portion 2; an operation portion 3 continuously connected to a proximal end of the insertion portion 2; and a universal cord 4 extended from the operation portion 3. An end portion of the universal cord 4 is provided with an endoscope connector (not shown) connected to a light source apparatus not shown that is an external apparatus.

The insertion portion 2 is a part inserted to a portion to be observed, such as in a body, and is provided with a distal end portion 2a, a bending portion 2b, and a rigid tube portion 2c in order from a distal end side. The distal end portion 2a is made of, for example, stainless steel that is a rigid member. The bending portion 2b is configured to bend in, for example, four vertical and horizontal directions relative to an insertion axis direction. The rigid tube portion 2c is formed by a metal tube member such as stainless steel.

Note that it is only necessary that the bending portion 2b can be bent in at least two directions relative to the insertion axis direction. In the following description, a configuration for bending in the vertical direction and a configuration for bending in the horizontal direction are substantially the same in a configuration in which the bending portion 2b is bent in four vertical and horizontal directions. Therefore, the configuration for bending in the vertical direction will be mainly described.

The bending portion 2b mainly includes a bending piece set (not shown) and a bending rubber 2g. The bending piece set is formed by pivotably connecting a plurality of bending pieces not shown, and the bending piece set bends vertically and horizontally. The bending rubber 2g is an outer skin with predetermined elastic force, covering an outer circumference of the bending piece set.

The elastic force of the bending rubber 2g acts as resistance force in bending the bending portion 2b and acts as restoring force for restoring the bending portion 2b to a straight line state when the bending portion 2b is in a bending state.

A signal cable, an illumination light guide, an air feeding tube, a water feeding tube, and the like described later are inserted into the insertion portion 2.

Note that the insertion portion 2 in the description above is a so-called rigid insertion portion continuously connecting the distal end portion 2a, the bending portion 2b, and the rigid tube portion 2c. However, the insertion portion 2 is not limited to the rigid insertion portion and may be a flexible insertion portion continuously connecting the distal end portion 2a, the bending portion 2b, and a flexible tube portion 2*d* with flexibility. A treatment instrument channel tube and the like may be inserted into the insertion portion 2.

A rubber boot 7 that is an exterior member is provided on a proximal end side of the operation portion 3. The rubber boot 7 is an elastic member with predetermined repulsion and includes an elastic holding portion 7*a* and an elastic fixing portion 7*b*. The elastic holding portion 7*a* has a function of elastically holding an angle lever 12, and the elastic fixing portion 7*b* has a function of blocking an opening 8*m* of a frame 8.

The operation portion 3 is provided with a bending operation member 5 and a semi-fixation mechanism switch operation member 6.

The bending operation member 5 includes, for example, a joy-stick-type angle lever 12 as a bending operation portion for remotely operating the bending portion 2*b*. The angle lever 12 is provided to protrude from the elastic holding portion 7*a* of the rubber boot 7 included in the operation portion 3. The angle lever 12 causes the bending portion 2*b* to move while changing a bending angle in one of the four vertical and horizontal directions along with a change in a tilt direction and a change in a tilt angle.

On the other hand, the semi-fixation mechanism switch operation member 6 includes, for example, a switch lever 31 as a semi-fixation operation portion for switching and operating in one of a semi-fixation state and a semi-fixation release state. The switch lever 31 can be freely switched to positions indicated by a solid line and a dashed line, for example. The switch lever 31 sets a semi-fixation mechanism to the semi-fixation release state at the position of the solid line and sets the semi-fixation mechanism to the semi-fixation state at the position of the dashed line.

The semi-fixation mechanism can cause the bending portion 2*b* to perform bending motion along with tilt operation of the angle lever 12 in the semi-fixation state and can hold a tilt operation position of the angle lever 12 when a finger is separated from the angle lever 12 during the bending operation. That is, the bending portion 2*b* is in an active bending state against restoring force or the like of the bending rubber 2*g* when the finger is separated from the angle lever 12, and the bending state at the time of the separation of the finger is maintained.

On the other hand, although the semi-fixation mechanism can of course cause the bending portion 2*b* to perform the bending motion along with the tilt operation of the angle lever 12 in the semi-fixation release state, the tilt operation position of the angle lever 12 cannot be held when the finger is separated from the angle lever 12 during the bending operation. That is, the bending portion 2*b* changes to a passive bending state when the finger is separated from the angle lever 12, and the restoring force from the bending rubber 2*g*, external force from outside, and the like enable the bending motion.

Note that an arrangement position of the angle lever 12 and an arrangement position of the switch lever 31 are examples. Although the bending directions of the bending portion 2*b* are four vertical and horizontal directions, the bending directions of the bending portion 2*b* are not limited to the four directions, and a configuration for bending in two vertical directions may be adopted.

A configuration of the operation portion 3 including the bending operation member 5 and the semi-fixation mechanism switch operation member 6 will be described with reference to FIGS. 3A and 3B.

The frame 8 is installed on an inner surface of a housing (not shown) that is an exterior member of the operation portion 3 provided on the proximal end side of the insertion portion 2, and a bending operation unit 10 is provided on the frame 8.

The bending operation unit 10 includes the bending operation member 5, an operation force reduction portion 20, and the semi-fixation mechanism switch operation member 6.

The frame 8 has, for example, a cylindrical shape and includes: an insertion portion installation portion 8*a* provided closer to a bottom surface 8*b*; and a bending mechanism attachment portion 8*c* provided closer to the opening 8*m*. The frame 8 may have an integrated configuration of the insertion portion installation portion 8*a* and the bending mechanism attachment portion 8*c*, or the insertion portion installation portion 8*a* and the bending mechanism attachment portion 8*c* may be integrated with a pipe-shaped frame body (not shown) by screwing, bonding, an adhesive, or the like.

A proximal end portion 2*r* of the insertion portion 2 is installed on the insertion portion installation portion 8*a*, and the proximal end portion 2*r* is integrated and fixed to the insertion portion installation portion 8*a*. The elastic fixing portion 7*b* of the rubber boot 7 is fixed to the opening 8*m* in a watertight manner. The bending mechanism attachment portion 8*c* includes an attachment portion body 8*d* and a lid portion 8*e*.

The attachment portion body 8*d* is provided with a bending mechanism installation portion 8*f* and a frame fixing portion 8*g*. The frame fixing portion 8*g* is a circular plate portion with a predetermined thickness, in which one end surface side is formed by a plane, and the bending mechanism installation portion 8*f* protrudes from the other end surface side.

An outer circumferential surface of the frame fixing portion 8*g* is an integrated surface and is integrated and fixed to an inner circumferential surface of the frame 8 by bonding using a solder or the like or by adhesion using an adhesive.

The bending mechanism installation portion 8*f* is, for example, a columnar center convex portion protruding at a predetermined height from a center of the other end surface of the frame fixing portion 8*g*. The bending mechanism installation portion 8*f* is provided with a first hemisphere concave portion 8*h*1 and a tilt relief hole 8*k*.

The first hemisphere concave portion 8*h*1 includes a circular opening on a bending mechanism installation portion end surface. The tilt relief hole 8*k* is a tapered center axis direction through hole connecting the first hemisphere concave portion 8*h*1 and the outside and includes an opening on a center end surface of the frame fixing portion 8*g*. A diameter dimension of the tilt relief hole 8*k* continuously increases toward the opening.

Note that a plurality of through holes with axes parallel to a center axis may be provided on the frame fixing portion 8*g* to reduce the weight of the bending mechanism attachment portion 8*c*.

On the other hand, the lid portion 8*e* is a columnar body similar to the bending mechanism installation portion 8*f* and is provided with a second hemisphere concave portion 8*h*2 and a swing relief hole 8*n*. The second hemisphere concave portion 8*h*2 includes a circular opening on one end surface. The swing relief hole 8*n* is a tapered center axis direction through hole connecting the second hemisphere concave portion 8*h*2 and the outside and includes an opening on the other end surface. A diameter dimension of the swing relief hole 8*n* continuously increases toward the opening.

Note that the lid portion 8*e* is integrated and fixed to an end surface of the bending mechanism installation portion 8*f* through, for example, screw fixation. In this case, a counterbore and a screw relief hole are formed on the lid portion 8e, and a concave portion provided with a female screw is formed on the bending mechanism installation portion 8f.

When the lid portion 8e is fixed to the bending mechanism installation portion 8f, a spherical body (see sign 13) described later is arranged in advance on the first hemisphere concave portion 8h1, and then the lid portion 8e is fixed by a screw. As a result, the spherical body 13 is arranged in a freely movable manner in a spherical body installation portion 8q formed by combining the first hemisphere concave portion 8h1 and the second hemisphere concave portion 8h2.

The bending operation member 5 includes: the angle lever 12 that provides pulling force to bending wires 11 that are pulling members; the spherical body 13 installed in the spherical body installation portion 8q; and a swing frame 14.

The spherical body 13 is provided with a lever connection portion on one side end portion of an axis passing through the center of the spherical body 13 and is provided with a swing axis connection portion on the other side end portion. The lever connection portion and the swing axis connection portion are concave portions and female screw portions.

In the present embodiment, the bending wires 11 include an upper bending wire 11u and a lower bending wire 11d. A distal end of the upper bending wire 11u is fixed to a predetermined site of a distal end bending piece (not shown) of the bending piece set included in the bending portion 2b. A distal end of the lower bending wire 11d is fixed to a predetermined site of the distal end bending piece. On the other hand, a proximal end of the upper bending wire 11u and a proximal end of the lower bending wire 11d are fixed to wire locking members 15 described later.

The angle lever 12 is a bending operation portion and includes, for example, a metal lever body 12a and a hemispherical metal finger hook portion 12b. The finger hook portion 12b is fixed to one end portion of the lever body 12a protruding from the elastic holding portion 7a of the rubber boot 7.

The other end portion of the lever body 12a is a spherical body connection portion 12c provided with a male screw (not shown). The male screw of the spherical body connection portion 12c is screwed to the lever connection portion of the spherical body 13 installed in the spherical body installation portion 8q and integrated and fixed by, for example, adhesion.

As a result, the spherical body 13, the swing frame 14 movable in the spherical body installation portion 8q along with the operation of the angle lever 12 includes a connection axis 14a, a cross shape frame portion (hereinafter, written as a cross frame) 14b, and an operation force reduction portion connection portion 14c.

The connection axis 14a is a center rod portion with a circular cross section protruding at a predetermined height from the center of one end surface of the cross frame 14b. On the other hand, the operation force reduction portion connection portion 14c is, for example, a columnar center convex portion protruding at a predetermined height from the center of the other end surface of the cross frame 14b.

An end portion of the connection axis 14a is provided with a male screw (not shown) screwed to the swing axis connection portion of the spherical body 13. The male screw of the connection axis 14a is screwed to the swing axis connection portion of the spherical body 13 installed in the spherical body installation portion 8q and integrated and fixed by, for example, adhesion.

As a result, when the spherical body 13 is moved in the spherical body installation portion 8q, the connection axis 14a integrated with the spherical body 13 also moves, and the cross frame 14b swings.

The operation force reduction portion connection portion 14c is provided with a sphere portion connection portion 14d and a swing relief hole 14e for arranging a first connection sphere portion 23 of the operation force reduction portion 20 described later in a freely movable manner.

The sphere portion connection portion 14d includes, for example, a connection portion hole 14f and a stopping member 14g fixed to the connection portion hole 14f. The connection portion hole 14f is formed from a side circumferential surface of the operation force reduction portion connection portion 14c, with an axis orthogonal to a center axis of the swing frame 14 as a center axis, and a bottom portion is hemispherical. The first connection sphere portion 23 of the operation force reduction portion 20 passes through the connection portion hole 14f and is guided to the hemispherical bottom surface.

The stopping member 14g is a rod-like member and is integrated and fixed to a predetermined position in the connection portion hole 14f by, for example, adhesion. A distal end surface of the stopping member 14g is formed as a concave spherical surface.

That is, the sphere portion connection portion 14d is formed by combining the hemispherical bottom surface of the connection portion hole 14f and the distal end surface of the stopping member 14g in the concave spherical surface shape.

The operation force reduction portion connection portion 14c includes an opening of the swing relief hole 14e on an end surface. The swing relief hole 14e is a tapered center axis direction through hole connecting the sphere portion connection portion 14d and the outside, and a diameter dimension continuously increases toward the opening.

Sign 14c denotes a notch groove. A first connection axis 24a of the operation force reduction portion 20 passes through the notch groove 14c when the first connection sphere portion 23 of the operation force reduction portion 20 is arranged from a side orthogonal to an operation portion longitudinal axis 3a toward the hemispherical bottom surface of the connection portion hole 14f.

Note that the sphere portion connection portion 14d may be formed by combining a first hemisphere concave portion and a second hemisphere concave portion like the configuration of the spherical body installation portion 8q.

The cross frame 14b includes an upper arm 14bu, a lower arm 14bd, a left arm (not shown), and a right arm (not shown). The upper arm 14bu, the lower arm 14bd, the left arm, and the right arm are provided to radially protrude from a side circumferential surface of the operation force reduction portion connection portion 14c, and in the present embodiment, intervals are 90 degrees in a circumferential direction.

In the present embodiment, an end portion of the upper arm 14bu is provided with a wire insertion hole 14h and a locking concave portion 14k. The wire insertion hole 14h is a through hole in which the upper bending wire 11u is arranged in a loosely fitted state and has openings on one surface and the other surface of the upper arm 14bu.

The locking concave portion 14k is a depression formed on one surface side of the upper arm 14bu. The wire locking portion 15, to which the other end of the upper bending wire 11u is integrated and fixed, is installed in the locking concave portion 14k. A center axis of the locking concave portion 14k and a center axis of the wire insertion hole 14h are coaxial.

An end portion of the lower arm 14bd is provided with a wire insertion hole 14h and a locking concave portion 14k as in the upper arm 14bu. Therefore, one surface and the other surface of the lower arm 14bd include openings of the wire insertion hole 14h. The wire locking portion 15 fixed to the lower bending wire 11d is installed on a depression of the locking concave portion 14k provided on one surface of the lower arm 14bd.

The upper bending wire 11u and the lower bending wire 11d are pulled and relaxed by inclination of the upper arm 14bu and the lower arm 14bd when the swing frame 14 is swung about the center of the spherical body 13 along with the tilt operation of the angle lever 12.

That is, the swing frame 14 swings about the spherical body 13 along with the tilt operation of the angle lever 12. The spherical body 13 is a fulcrum of the bending operation member 5.

The operation force reduction portion 20 is provided between the bending operation member 5 and the semi-fixation mechanism switch operation member 6. The operation force reduction portion 20 includes a bending operation portion forming portion (hereinafter, written as a first reduction portion) 21, a semi-fixation mechanism portion forming portion (hereinafter, written as a second reduction portion) 22, and a compression coil spring (hereinafter, abbreviated as a spring) 29 that is an elastic member.

The first reduction portion 21 is provided with the first connection sphere portion 23 that serves as a first end portion, a first outward flange (hereinafter, abbreviated as a first flange) 24, and a slide axis 25.

The first connection sphere portion 23 is a spherical portion and is provided on the end portion of the first connection axis 24a protruded from the first flange 24. The first connection sphere portion 23 is arranged in a freely movable manner in the sphere portion connection portion 14d of the bending operation member 5 described above.

The second reduction portion 22 is provided with a cylindrical portion 26, a second outward flange (hereinafter, abbreviated as a second flange) 27, and a second connection sphere portion 28 that serves as a second end portion.

The second connection sphere portion 28 is a spherical portion and is provided on an end portion of a second connection axis 27a protruded from the second flange 27. The second connection sphere portion 28 is arranged in a freely movable manner in a second sphere portion connection portion 39 described later of the semi-fixation mechanism switch operation member 6 described above.

The cylindrical portion 26 protrudes at a predetermined height from one surface of the second flange 27 and is provided with a center hole 26h along a center axis of the second reduction portion. An outer diameter of the cylindrical portion 26 is a predetermined dimension smaller than a coil inner diameter of the spring 29. An inner diameter of the center hole 26h is set in a predetermined fitting manner in consideration of an outer diameter dimension of the slide axis 25.

The spring 29 is arranged on an outer circumferential surface of the cylindrical portion 26. The spring 29 has preset elastic force, and a natural length is set to a predetermined height.

The operation force reduction portion 20 is formed by inserting the slide axis 25 into the center hole 26h of the cylindrical portion 26 in a state that the spring 29 is arranged on the outer circumferential surface of the cylindrical portion 26. With this configuration, the first reduction portion 21 and the second reduction portion 22 can freely move forward and backward along a longitudinal axis connecting the center of the first connection sphere portion 23 and the center of the second connection sphere portion 28.

Figure 3A:
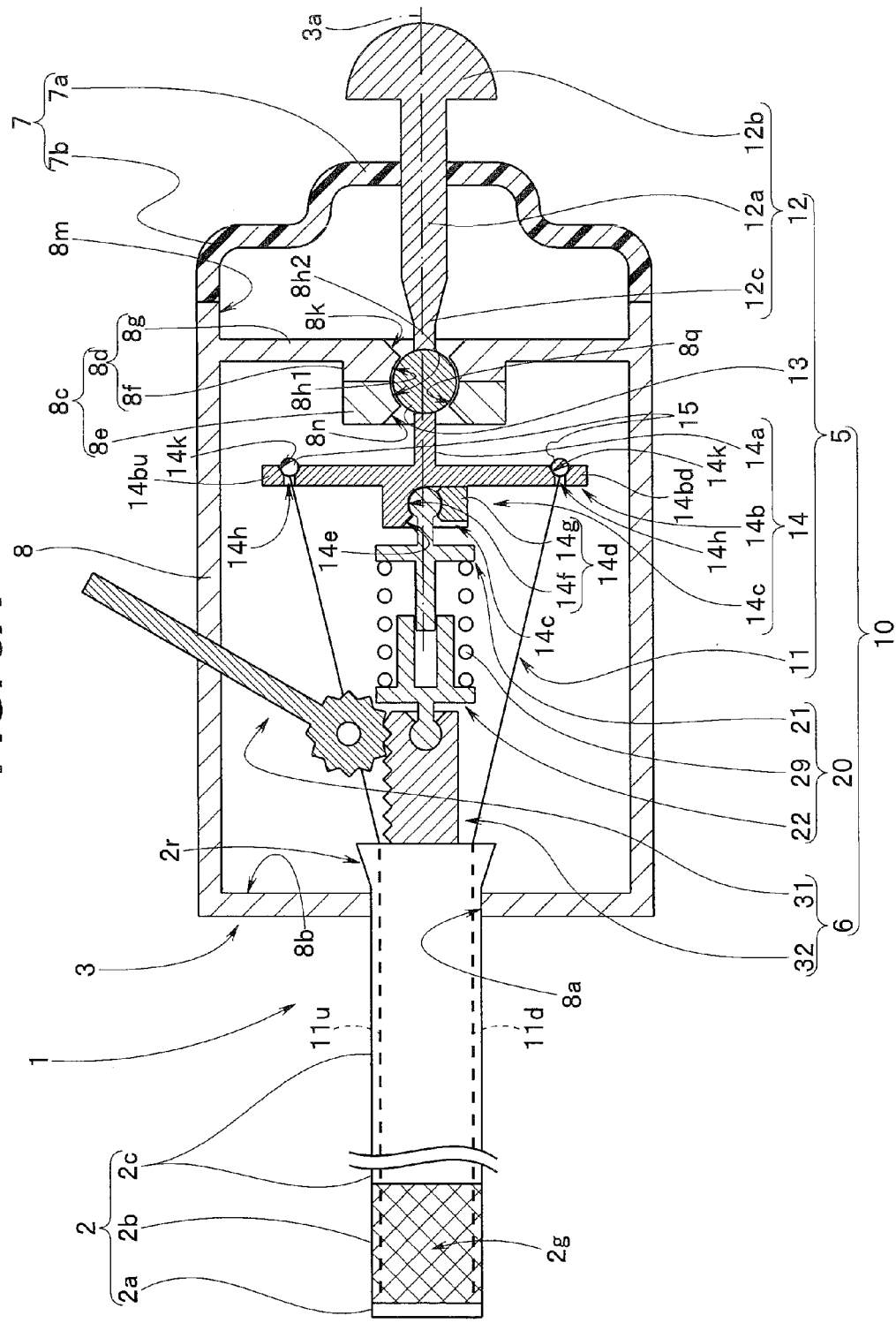
FIG. 3A is a diagram describing an example of configuration in the operation portion including an operation force reduction portion, the semi-fixation mechanism switch operation member, and the bending operation member.

As shown in FIG. 3A, when the bending portion 2b of the insertion portion 2 is in a straight line state (neutral position), the center of the second connection sphere portion 28, the center of the first connection sphere portion 23, and the center of the spherical body 13 are arranged in a straight line on the operation portion longitudinal axis 3a, and the spring 29 has a natural length. In this case, one of seats of the spring 29 is arranged on the other surface side of the first flange 24, and the other seat of the spring 29 is arranged on one surface side of the second flange 27.

Note that one of the seats and the other seat of the spring 29 may not be in contact with the other surface side of the first flange 24 and the one surface side of the second flange 27, respectively.

Figure 3B:
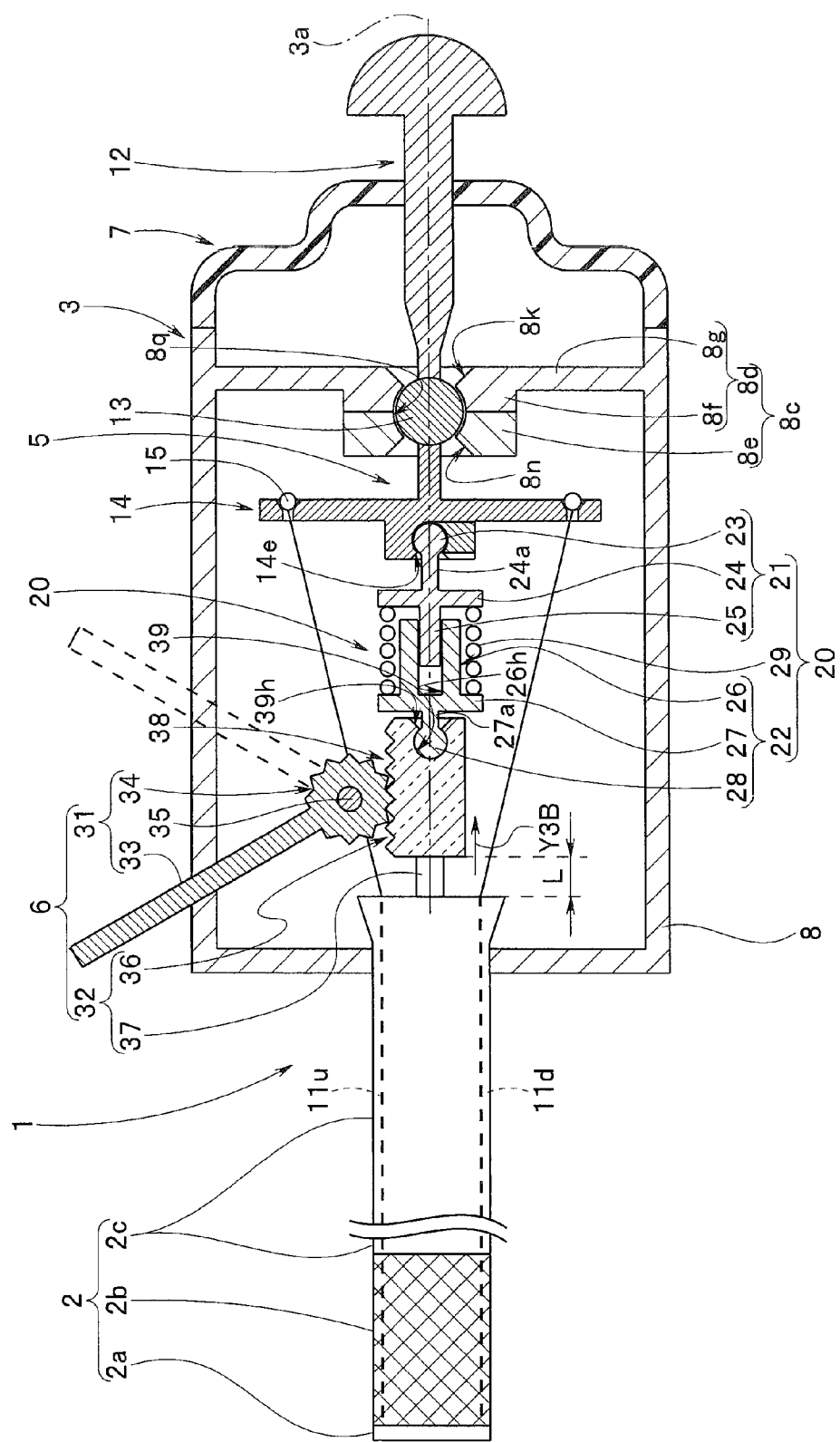
FIG. 3B is a diagram describing a configuration in the operation portion in which the semi-fixation mechanism switch operation member is in a semi-fixation state.

As shown in FIGS. 3A and 3B, the semi-fixation mechanism switch operation member 6 mainly includes a switch lever 31 and a slide member 32.

The switch lever 31 includes a lever body 33 and a pinion gear portion 34 made of, for example, metal. The pinion gear portion 34 is integrated with an end portion positioned in the operation portion. The switch lever 31 is pivotable about an axis 35 and can rotate clockwise and counterclockwise.

Note that a hemispherical finger hook portion may be provided on an end portion on an opposite side of the switch lever 31, for example.

The slide member 32 includes a slide member body (hereinafter, abbreviated as a slide body) 36 and a key 37.

The key 37 is an elongated guide member in a rectangular solid shape and is fixed to a ground plane not shown integrated with the frame 8. The key 37 is provided parallel to the operation portion longitudinal axis 3a of the operation portion 3.

The slide body 36 is provided with: a key groove (not shown) in which the key 37 is arranged; a rack 38 engaged with the pinion gear portion 34; and the second sphere portion connection portion 39. The second connection sphere portion 28 is arranged on the second sphere portion connection portion 39 in a freely movable manner. Sign 39h denotes a second connection sphere portion relief hole and is a tapered center axis direction through hole connecting the second sphere portion connection portion 39 and the outside. A diameter dimension of the hole continuously increases toward the opening.

The key groove of the slide body is arranged on the key 37, and the slide body 36 can freely move forward and backward in the direction of the operation portion longitudinal axis 3a. The pinion gear portion 34 and the rack 38 form a rack and pinion mechanism.

Therefore, when the switch lever 31 is rotated counterclockwise about the axis 35 and is switched from a position indicated by a dashed line of FIG. 3B to a position indicated by a solid line of FIG. 3B, the engagement of the pinion gear portion 34 and the rack 38 is changed, and the slide body 36 is gradually moved in a direction of an arrow Y3B that is the direction of the operation portion longitudinal axis 3a.

Note that when the switch lever 31 is rotated clockwise that is an opposite direction, the rack and pinion mechanism moves the slide body 36 in an opposite direction of the direction of the arrow Y3B.

When the bending portion 2b is in the straight line state, the slide body 36 is moved by a distance L in the direction of the arrow Y3B by switching the switch lever 31 from the position indicated by the dashed line to the position indicated by the solid line. Along with the movement of the slide body 36, the second connection sphere portion 28 included in the operation force reduction portion 20 also approaches the first connection sphere portion 23 along the operation portion longitudinal axis 3a.

That is, as the second reduction portion 22 is moved toward the first reduction portion 21, the spring 29 installed between the first flange 24 and the second flange 27 is gradually compressed. When the spring 29 reaches a predetermined compressed state, the operation force reduction portion 20 is moved in the direction of the arrow Y3B.

As a result, an outer surface of the first connection sphere portion 23 comes into contact with an inner surface of the sphere portion connection portion 14d, and then the first connection sphere portion 23 presses the sphere portion connection portion 14d by predetermined pressing force to set the semi-fixation state.

That is, the semi-fixation mechanism switch operation member 6 is formed by including the operation force reduction portion 20 in the switch lever 31 and the slide member 32 in the endoscope 1 of the present embodiment.

Note that when the spring 29 has the natural length shown in FIG. 3A, the urging force is not acting on the other surface of the first flange 24 and one surface of the second flange 27 from the seats of the spring 29, respectively. In this state, the first connection sphere portion 23 is in a non-pressing state relative to the sphere portion connection portion 14d and can freely move. The state will be called a semi-fixation release state with respect to the semi-fixation state.

The second sphere portion connection portion 39 is formed by combining a connection portion hole with a hemispherical bottom surface and a stopping member with a distal end surface in a concave spherical surface shape as in the sphere portion connection portion 14d described above or by combining a first hemisphere concave portion and a second hemisphere concave portion as in the spherical body installation portion 8q described above, for example.

Here, working of the operation portion 3 in the semi-fixation release state and working of the operation portion 3 in the semi-fixation state will be described. The working of the operation portion 3 in the semi-fixation release state will be described first.

Figure 4A:
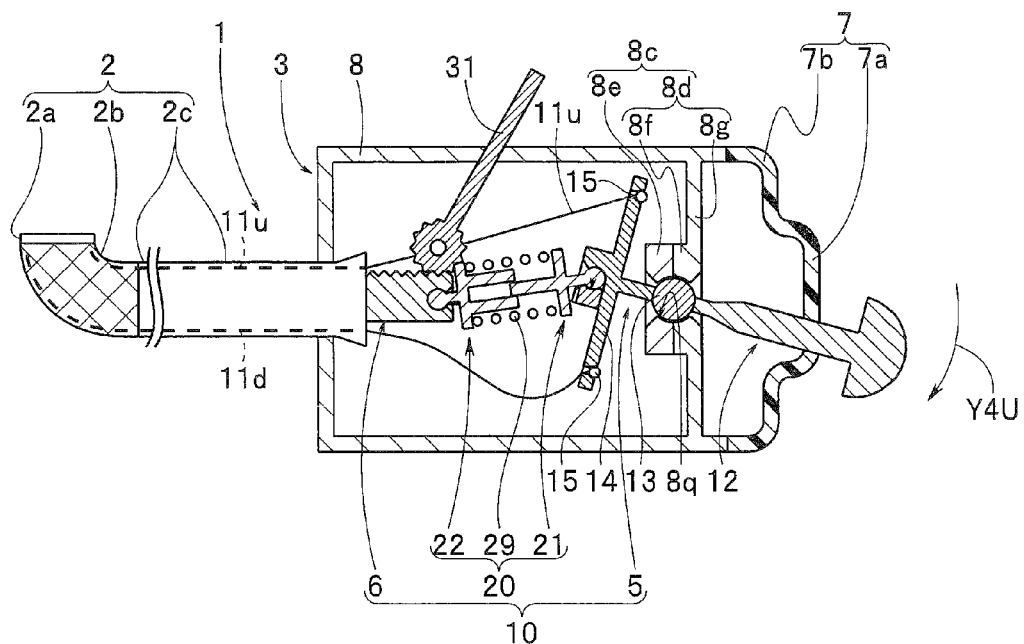
FIG. 4A is a diagram describing working of the endoscope in a semi-fixation release state.

In the semi-fixation release state of FIG. 3A, when a user tilts the angle lever 12 in, for example, a direction of an arrow Y4U as shown in FIG. 4A, the swing frame 14 is swung clockwise with the spherical body 13 as a fulcrum. As a result, the upper bending wire 11u installed on the upper arm 14bu is pulled as shown in FIG. 4A. On the other hand, the lower bending wire 11d is relaxed, and the bending portion 2b is bent in an upper direction as shown in FIG. 4A.

Figure 5:
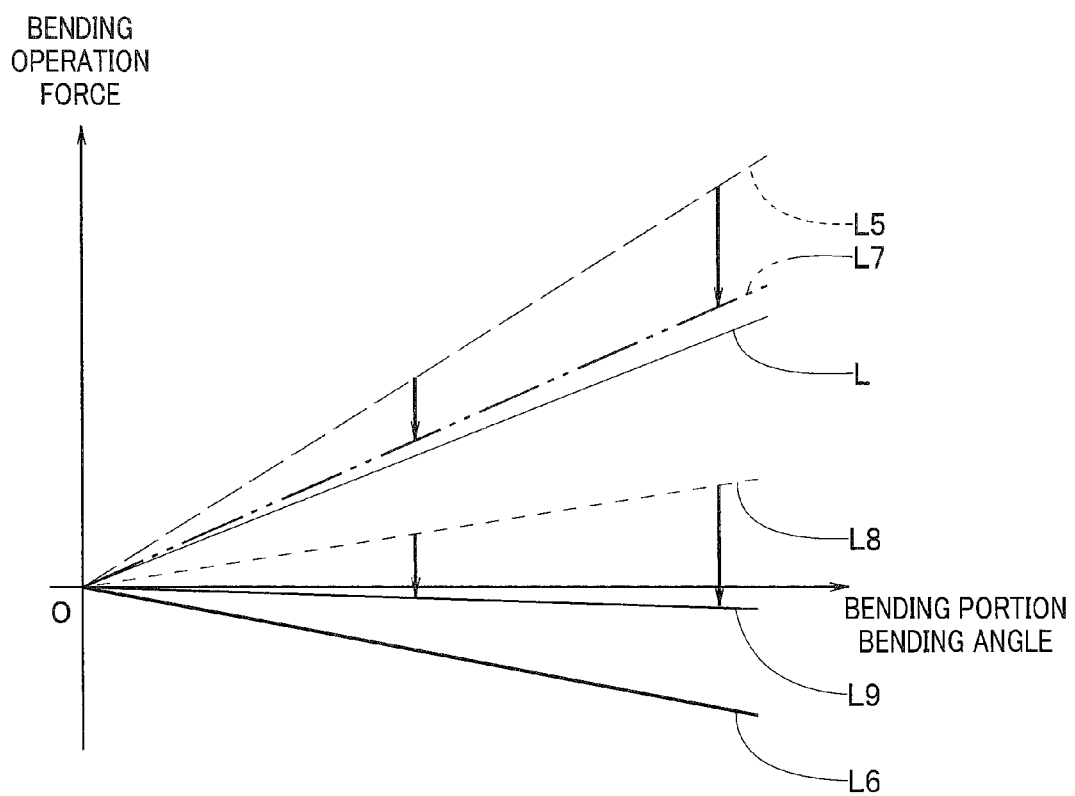
FIG. 5 is a diagram describing a relationship between a bending angle of a bending portion, bending operation force for operating a bending operation member, and reaction force urging force in the endoscope of the present application.

In this case, the user operates the angle lever 12 by bending operation force indicated by a first dashed line L5 of FIG. 5 against bending portion resistance force that is a combination of the restoring force of the bending rubber 2g and the resistance force from the endoscope built-in parts as described above. Therefore, the bending operation force for operating the angle lever 12 increases with an increase in the bending angle of the bending portion 2b as described above.

That is, an operational feeling as in the conventional endoscope can be obtained in the operation portion 3 in the semi-fixation release state. Furthermore, when the finger is separated from the angle lever 12, the bending portion 2b enters the passive bending state, and the bending motion can be performed by the restoring force from the bending rubber 2g, the external force from the outside, and the like.

Next, the working of the operation portion 3 in the semi-fixation state will be described.

In the semi-fixation state shown in FIG. 3B, the endoscope 1 of the present embodiment is provided with the operation force reduction portion 20 and the semi-fixation mechanism switch operation member 6 including the operation force reduction portion 20 in the operation portion 3. Therefore, the endoscope 1 can hold the tilt operation position of the angle lever 12 when the finger is separated from the angle lever 12 during the bending operation, and the operation force of the angle lever 12 can be reduced to cause the bending portion 2b to perform the bending motion.

Figure 4B:
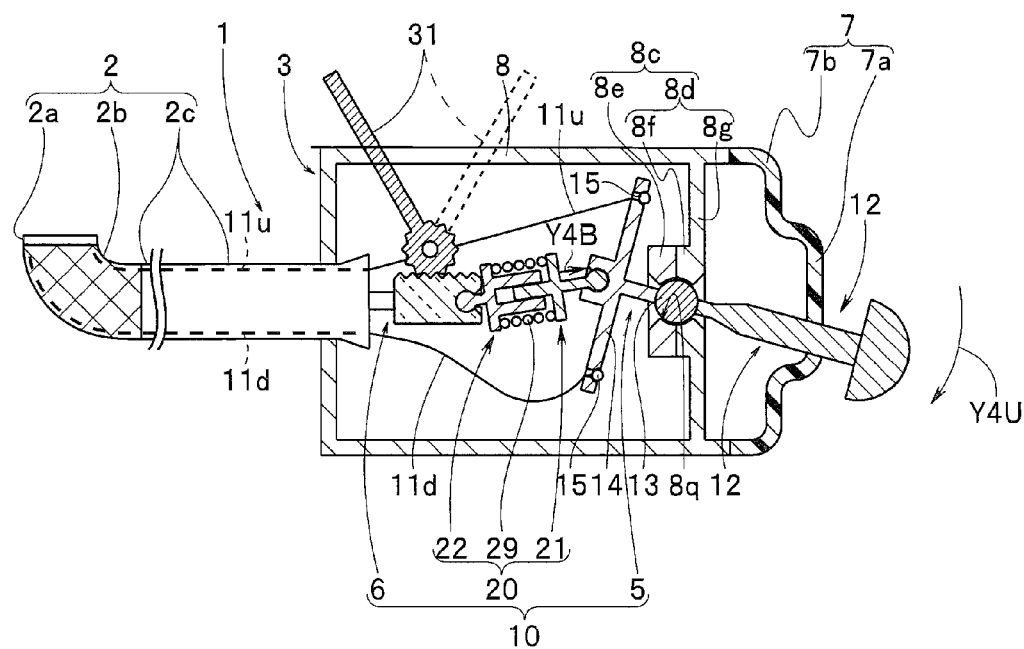
FIG. 4B is a diagram describing working of the endoscope in the semi-fixation state.

More specifically, in the semi-fixation state of FIG. 3B, when the user performs the tilt operation of the angle lever 12 in, for example, the direction of the arrow Y4U as shown in FIG. 4B, the swing frame 14 is swung clockwise with the spherical body 13 as a fulcrum. As a result, as a result, the upper bending wire 11u installed on the upper arm 14bu is pulled as shown in FIG. 4B. On the other hand, the lower bending wire 11d is relaxed, and the bending portion 2b is bent in the upper direction as shown in FIG. 4B.

In the present embodiment, at the same time as the inclination of the angle lever 12 and the rotation of the swing frame 14 clockwise, the operation force reduction portion 20 starts rotating counterclockwise with the second connection sphere portion 28 as a fulcrum. Consequently, a longitudinal axis 20a of the operation force reduction portion 20 inclines relative to the operation portion longitudinal axis 3a, and the urging force of the spring 29 of the operation force reduction portion 20 moves the first reduction portion 21 in a direction away from the second reduction portion 22, that is, a direction of an arrow Y4B.

Here, the urging force applied from the spring 29 to the first reduction portion 21 is provided as force for clockwise rotation of the swing frame 14 that rotates in conjunction with the angle lever 12. That is, when the angle lever 12 is tilted and operated to cause the bending portion 2b to perform the bending motion, the operation force reduction portion 20 provides the swing frame 14 with reaction force urging force (also written as assist force) that is rotation torque corresponding to predetermined urging force of the spring 29 and that assists the bending operation, thereby reducing the operation force of the angle lever 12.

Note that when the angle lever 12 is inclined in an opposite direction of the arrow Y4U to rotate the swing frame 14 counterclockwise in FIG. 4B, the operation force reduction portion 20 is rotated clockwise with the second connection sphere portion 28 as a fulcrum, and the longitudinal axis 20a of the operation force reduction portion 20 inclines in the opposite direction of the operation portion longitudinal axis 3a. As a result, urging force in a direction that separates the first reduction portion 21 away from the second reduction portion 22 is applied due to the urging force of the spring 29 of the operation force reduction portion 20. The urging force applied from the spring 29 to the first reduction portion 21 is provided as force for counterclockwise rotation of the swing frame 14 that rotates in conjunction with the angle lever 12.

In this way, when the angle lever 12 is tilted and operated to cause the bending portion 2b to perform the bending motion in the upper direction or the lower direction, the operation force reduction portion 20 can provide the reaction force urging force in the inclination direction of the swing frame 14 to reduce the operation force of the angle lever 12.

In other words, when the angle lever 12 is tilted and operated to bend the bending portion 2b in the semi-fixation state, the assist force for urging in the direction of the inclination of the swing frame 14 is applied from the spring 29 of the operation force reduction portion 20.

The angle lever 12 and the swing frame 14 are integrated and connected by the spherical body 13. The spherical body 13 is held by the spherical body installation portion 8*q* in a movable manner, and the angle lever 12 and the swing frame 14 rotate in conjunction about the spherical body 13. Therefore, the rotation torque around the center of the spherical body 13 generated by the urging force of the spring 19 of the operation force reduction portion 20 becomes reaction force urging force for reducing the operation force of the angle lever 12.

Rotational components generated around the center of the spherical body 13 increase with an increase in an absolute value of the rotation angle of the spherical body 13 when the angle lever 12 is inclined, and the rotation torque around the center of the spherical body 13 provided from the spring 19 of the operation force reduction portion 20 increases.

That is, the reaction force urging force provided by the operation force reduction portion 20 increases with an increase in the absolute value of the rotation angle of the spherical body 13 due to the operation of the angle lever 12 as indicated by a first solid line L6 of FIG. 5, and the operation torque necessary during the operation of the angle lever 12 is reduced by the amount of the reaction force urging force.

Therefore, when the user operates the angle lever 12 to increase the bending angle of the bending portion 2*b*, the user can perform the bending operation of the bending portion 2*b* based on bending operation force indicated by an alternate long and two short dashes line L7 that is equivalent to the bending operation force indicated by the first dashed line L5 minus the amount of the reaction force urging force indicated by the first solid line L6.

Furthermore, bending portion holding force indicated by a second dashed line L8 that is a combination of the restoring force of the bending rubber 2*g* and the resistance force of the endoscope built-in parts and that acts to restore an original state of the bent bending portion 2*b* also becomes equal to or smaller than 0 as indicated by a second solid line L9, because the reaction force urging force indicated by the first solid line L6 is provided during the bending operation.

Therefore, the bending portion holding force is equal to or smaller than 0 when the user separates the finger from the angle lever 12 during the bending operation. As a result, the tilt operation position of the angle lever 12 is held, and the bending state of the bending portion 2*b* is held in the state at the time of the separation of the finger from the angle lever 12.

In this way, according to the endoscope 1 of the present embodiment, the switch lever 31 can be switched and operated to easily obtain the semi-fixation state and the semi-fixation release state.

Therefore, the bending portion 2*b* can be bent in the semi-fixation release state as in a normal endoscope, and the switch lever 31 can be operated to make a switch to the semi-fixation state to hold the bending state of the bending portion 2*b* when the finger is separated from the angle lever 12.

The bending operation force in the semi-fixation state is smaller than in the semi-fixation release state due to the reaction force urging force provided from the operation force reduction portion 20. Therefore, bending operability improves, and slight bending operation in the semi-fixation state can be easily performed.

Note that the semi-fixation mechanism switch operation member 6 mainly includes the switch lever 31 and the slide member 32 in the embodiment described above. However, the semi-fixation mechanism switch operation member may be formed as shown in FIGS. 6A and 6B, and a semi-fixation mechanism switch operation member 6A may be switched and operated in the semi-fixation state and the semi-fixation release state.

Note that the same members as in the embodiment described above are designated with the same signs, and the description will not be repeated.

Figure 6A:
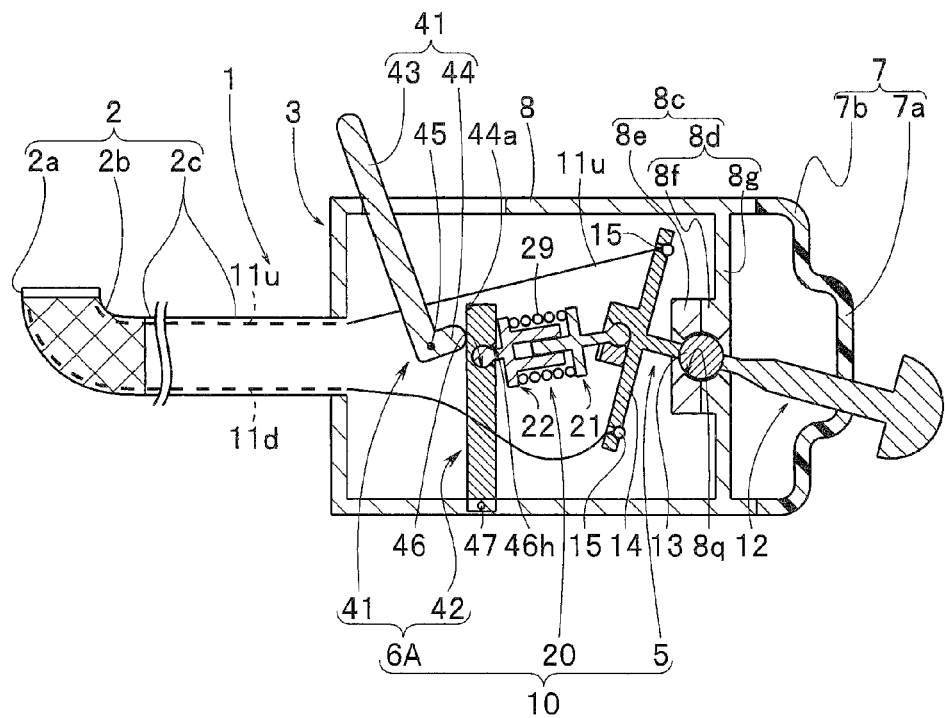
FIGS. 6A and 6B are diagrams describing another example of configuration of the semi-fixation mechanism switch operation member and are diagrams describing the semi-fixation state of the semi-fixation mechanism switch operation member.
Figure 6B:
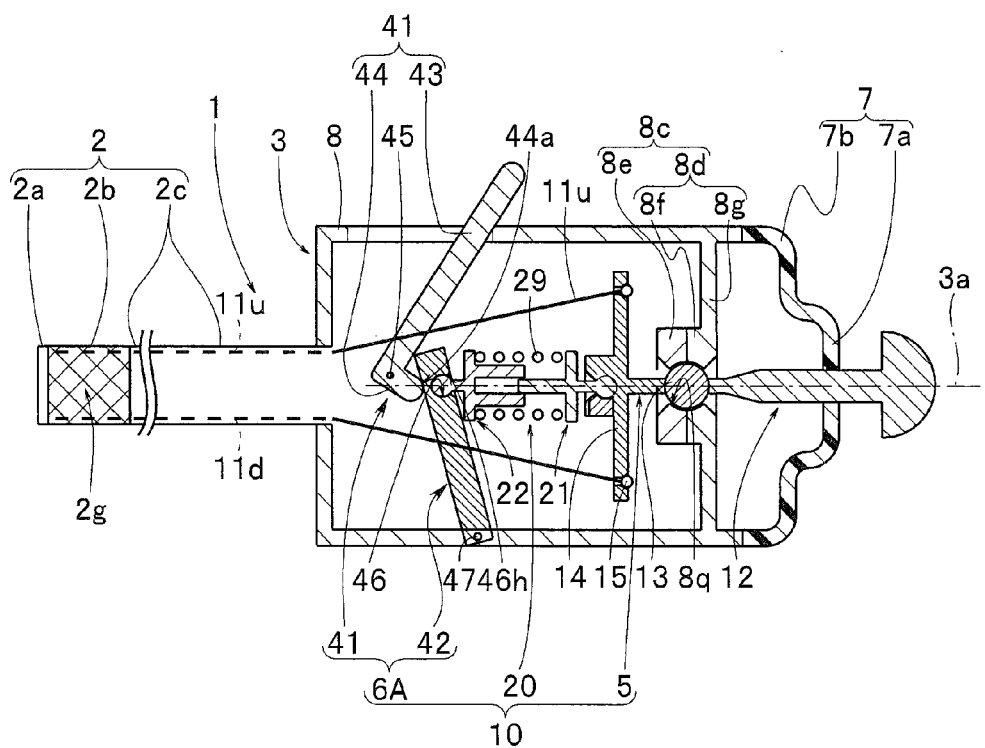

As shown in FIGS. 6A and 6B, the semi-fixation mechanism switch operation member 6A mainly includes a switch lever 41 and a lever member 42.

The switch lever 41 includes a lever body 43 and a contact arm portion 44 made of, for example, metal and is formed in an L-shape. That is, an axis of the contact arm portion 44 is substantially orthogonal to an axis of the lever body 43. The switch lever 41 is pivotable about a first axis 45 provided at a bent part. In a state that the axis of the lever body 43 is orthogonal to the operation portion longitudinal axis 3*a*, the switch lever 41 is arranged in a neutral state in which the lever 41 does not rotate about the first axis 45. Note that the switch lever 41 may have a shape without the bent part, such as a straight line shape.

The lever member 42 is made of, for example, metal and includes a second sphere portion connection portion 46. The second connection sphere portion 28 is arranged on the second sphere portion connection portion 46 in a freely movable manner. Sign 46*h* denotes a second connection sphere portion relief hole which is a tapered through hole connecting the second sphere portion connection portion 46 and the outside. A diameter dimension of the hole continuously increases toward the opening. The lever member 42 is pivotable about a second axis 47.

An end portion of the lever member 42 away from the second sphere portion connection portion 46 is pivotably held by the second axis 47.

In the present embodiment, a curved surface portion 44*a* that serves as a lever member contact portion is provided on the contact arm portion 44 of the switch lever 41. The curved surface portion 44*a* can be arranged in contact with the other surface side of the lever member 42.

While the switch lever 41 is rotated and operated on an insertion portion side about the first axis 45, the curved surface portion 44*a* of the switch lever 41 is in contact with the other surface side of the lever member 42.

Therefore, when the lever member 42 starts rotating toward the angle lever 12 about the second axis 47, the second connection sphere portion 28 of the operation force reduction portion 20 arranged on the second sphere portion connection portion 46 is brought closer to the first connection sphere portion 23.

As a result, the second reduction portion 22 is moved toward the first reduction portion 21, and the spring 29 installed between the first flange 24 and the second flange 27 is changed to the compressed state as described above. The semi-fixation mechanism switch operation member 6A enters the semi-fixation state.

In the present embodiment, the switch lever 41 is rotated counterclockwise and enters the neutral state. Here, when the switch lever 41 is further rotated and operated counterclockwise beyond an inflection point, the urging force of the spring 29 holds the switch lever 41 in a state in which the switch lever 41 is in contact with one end of the opening.

On the other hand, when the switch lever 41 is rotated and operated from the semi-fixation state shown in FIG. 6A toward the angle lever 12 about the first axis 45 as shown in FIG. 6B, the semi-fixation mechanism switch operation member 6A is switched from the semi-fixation state to the semi-fixation release state.

In this case, the curved surface portion 44a is moved in a direction away from the other surface side of the lever member 42 along with the rotation of the switch lever 41. Consequently, the pressing force of the lever member 42 is gradually reduced, and the spring 29 in the compressed state between the first flange 24 and the second flange 27 gradually changes to an extended state. That is, the second reduction portion 22 of the operation force reduction portion 20 is moved away from the first reduction portion 21.

As a result, the lever member 42 including the second sphere portion connection portion 46 provided with the second connection sphere portion 28 of the operation force reduction portion 20 is rotated toward the insertion portion 2 about the second axis 47 due to the urging force of the spring 29, and the spring 29 is returned to substantially the natural length.

Note that in this case, the switch lever 41 is rotated clockwise and enters the neutral state. When the switch lever 41 is further rotated and operated clockwise beyond the inflection point, the urging force of the spring 29 holds the switch lever 41 in a state in which the switch lever 41 is in contact with the other end of the opening.

An assist force adjustment mechanism will be described with reference to FIG. 7.

As described, the rotation torque (also written as reaction force urging force) from the spring 29 can be provided to the swing frame 14 to reduce the operation force of the angle lever 12.

With this structure, when the reaction force urging force (written as assist force) becomes greater than the bending operation force for operating the angle lever 12, the lever 12 falls down before the operation of the angle lever 12.

On other hand, even if the bending operation force for operating the angle lever 12 is greater than the assist force, the operation force may not be sufficiently reduced unless sufficiently large assist force is provided.

The assist force can be realized by changing an equipment length of the spring of the operation force reduction portion 20. However, when the length of the equipment length is adjusted, an amount of change in the assist force is small compared to an amount of adjustment. Therefore, in order to adjust the equipment length to obtain desired assist force, the amount of adjustment needs to be large to increase the amount of change in the assist force. However, the size of the operation portion needs to be increased to obtain the desired assist force by adjusting the equipment length of the spring. Therefore, a small assist force adjustment mechanism is desired.

Figure 7:
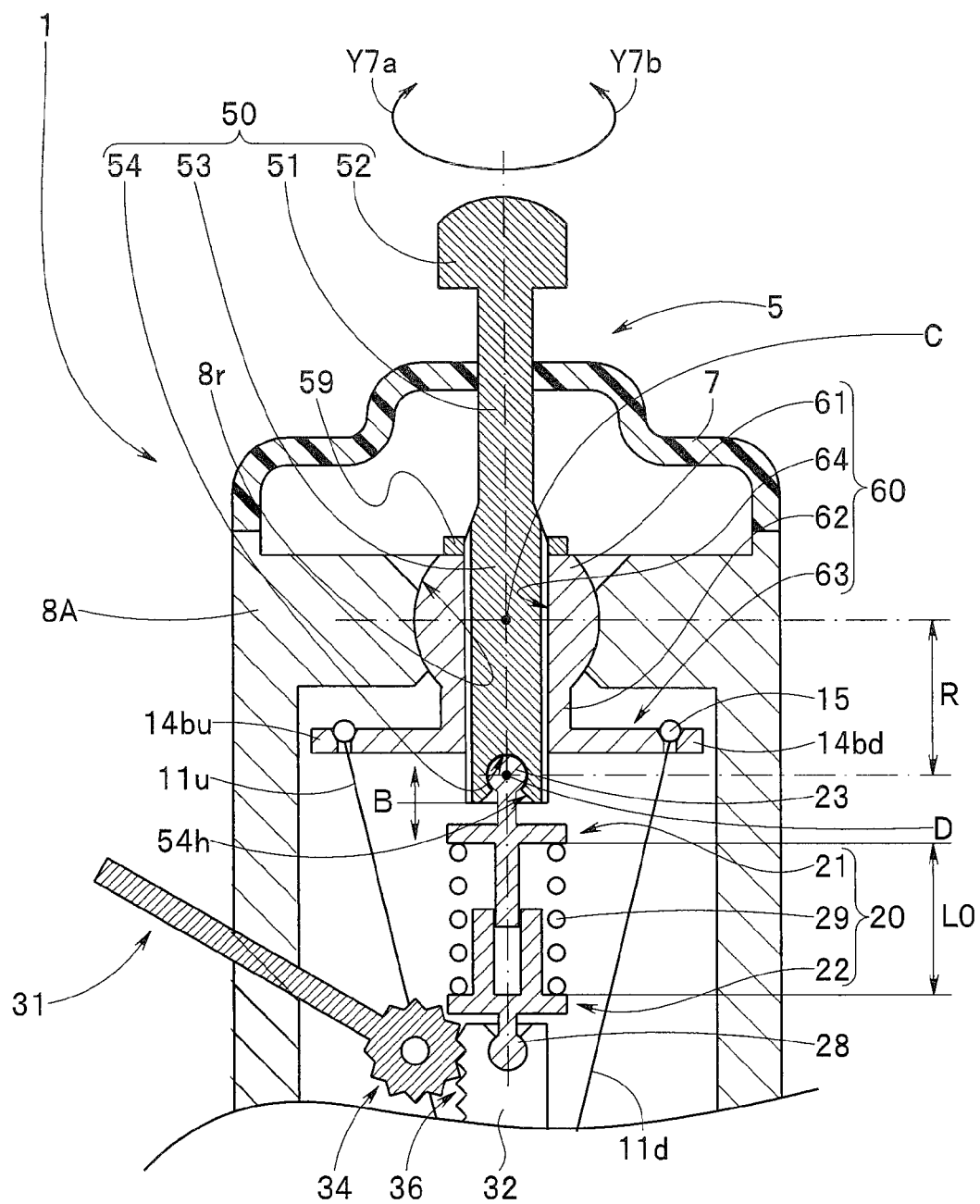
FIG. 7 is a diagram describing a mechanism of adjusting assist force of the operation force reduction portion included in the semi-fixation mechanism switch operation member.

As shown in FIG. 7, a frame 8A of the present embodiment is provided with a sphere portion installation portion 8r. An inner surface of the sphere portion installation portion 8r is a spherical concave portion.

The bending operation member 5 of the present embodiment includes: a combined angle lever 50 that provides pulling force to the bending wires 11 and that also serves as an assist force adjustment portion; a swing frame 60 provided with a spherical portion 61 installed in the sphere portion installation portion 8r; and a looseness prevention nut 59. The assist force adjustment mechanism includes the combined angle lever 50 and the swing frame 60.

The combined angle lever 50 includes: a lever body 51 that is a bending operation portion and that is made of, for example, metal; a metal finger hook portion 52 that is, for example, hemispherical and that includes a plane portion on an outer circumference side surface; and a lever adjustment portion 53 provided with a male screw on an outer circumferential surface. The finger hook portion 52 is fixed to one end portion of the lever body 51 protruding from the rubber boot 7.

The lever adjustment portion 53 provided with the male screw is provided on the other end portion side of the lever body 51, and a diameter is greater than that of the lever body 51. An operation force reduction portion connection portion 54 provided with the first connection sphere portion 23 of the operation force reduction portion 20 in a freely movable manner is provided on an end surface side of the lever adjustment portion 53.

The operation force reduction portion connection portion 54 is formed by combining a connection portion hole having a hemispherical bottom surface and a stopping member having a distal end surface in a concave spherical surface shape as in the sphere portion connection portion 14d or by combining a first hemisphere concave portion and a second hemisphere concave portion as in the spherical body installation portion 8q, for example.

Sign 54h denotes a sphere portion relief hole which is a tapered through hole connecting the operation force reduction portion connection portion 54 and the outside, and a diameter dimension of the hole continuously increases toward the opening.

The swing frame 60 is provided with the spherical portion 61, a connection axis 62, a cross frame 63, and an adjustment hole 64.

The cross frame 63 includes the upper arm 14bu, the lower arm 14bd, a left arm (not shown), and a right arm (not shown). The upper arm 14bu, the lower arm 14bd, the left arm, and the right arm are provided to radially protrude from a side circumferential surface of the connection axis 62, and in the present embodiment, intervals are 90 degrees in a circumferential direction.

The spherical portion 61 is provided on an end portion of the connection axis 62. The spherical portion 61 has a spherical surface and is arranged in the sphere portion installation portion 8r in a freely movable manner. A looseness prevention nut installation surface is formed on a distal end side of the spherical portion 61.

The connection axis 62 protrudes from a center on one end surface side of the cross frame 63 and is a center convex portion with a circular cross section.

The adjustment hole 64 includes openings on the other end surface of the cross frame 63 and on the looseness prevention nut installation surface and is a through hole elongated in an axis direction of the connection axis 62. A female screw is formed on an inner circumferential surface of the adjustment hole 64. The male screw of the lever adjustment portion 53 is screwed and arranged on the female screw of the adjustment hole 64.

In the present embodiment, the finger hook portion 52 is rotated in a direction of an arrow Y7a or a direction of an arrow Y7b to move the lever adjustment portion 53 forward and backward in the axis direction of the angle lever, and an amount of protrusion of the distal end surface of the lever adjustment portion 53 from the other end surface of the cross frame 63 changes.

After the adjustment of the amount of protrusion of the distal end surface of the lever adjustment portion 53 from the other end surface of the cross frame 63, the looseness prevention nut 59 is fastened to the male screw provided on the lever adjustment portion 53 to hold the amount of protrusion of the distal end surface of the lever adjustment portion 53 protruded from the other end surface of the cross frame 63.

The other components are the same as in the embodiment described above. The same members are designated with the same signs, and the description will not be repeated.

According to the configuration, a radius R that is a distance between a point C and a point D is extended to increase the reaction force urging force.

In this case, an operator loosens the looseness prevention nut 59. The operator then rotates the finger hook portion 52 in the direction of the arrow Y7a. In this way, the amount of protrusion of the distal end surface of the lever adjustment portion 53 from the other end surface of the cross frame 63 is increased along with the rotation, and the radius R increases.

When the radius R reaches a desired value, the operator fastens the looseness prevention nut 59. In this way, the radius R is held at the desired value.

As a result, rotational moment (reaction force urging force) around the point C increases with an increase in the radius R. Furthermore, along with the increase in the amount of protrusion of the distal end surface of the lever adjustment portion 53 from the other end surface of the cross frame 63, an equipment length L0 of the spring is reduced, and the force of the spring 29 is increased.

In this way, the lever adjustment portion 53 is rotated to adjust the amount of protrusion of the distal end surface of the lever adjustment portion 53 from the other end surface of the cross frame 63. As a result, a compound effect of changing the radius R and the equipment length L0 of the spring can be obtained, and the force adjustment for significantly changing the reaction force urging force can be easily performed.

Therefore, the operation force can be easily adjusted according to a preference of the user.

An example of configuration of the endoscope including bending operation members and semi-fixation mechanism switch operation members provided on the operation portion in consideration of the operability will be described with reference to FIGS. 8 to 15.

Note that in the following description, the same members as in the embodiment described above are designated with the same signs, and the description will not be repeated.

Figure 8:
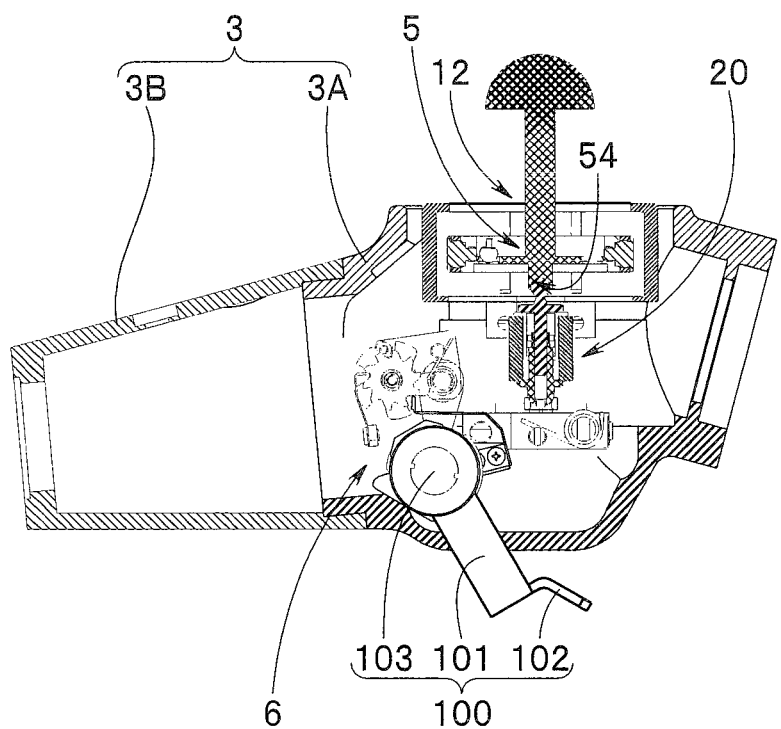
FIG. 8 is a diagram describing an example of configuration of the operation portion including the bending operation member on one surface side of the operation portion and including the semi-fixation mechanism switch operation member on the other surface side that is an opposite surface of one surface.

As shown in FIG. 8, the operation portion 3 of the endoscope 1 includes a front cover portion 3A and an operation portion body 3B. The bending operation member 5 and the semi-fixation mechanism switch operation member 6 are provided in the front cover portion 3A. The angle lever 12 of the bending operation member 5 protrudes from one surface side of the front cover portion 3A that is an upper surface in FIG. 8. A switch lever 100 of the semi-fixation mechanism switch operation member 6 is provided on the other surface of the front cover portion 3A that is a lower surface in FIG. 8 and that is an opposite surface of one surface.

The angle lever 12 is a joy stick type as described above and is tilted and operated. The switch lever 100 includes a lever body 101 and a finger contact portion 102, and the lever body 101 can be manually operated counterclockwise about a lever axis 103.

Figure 9:
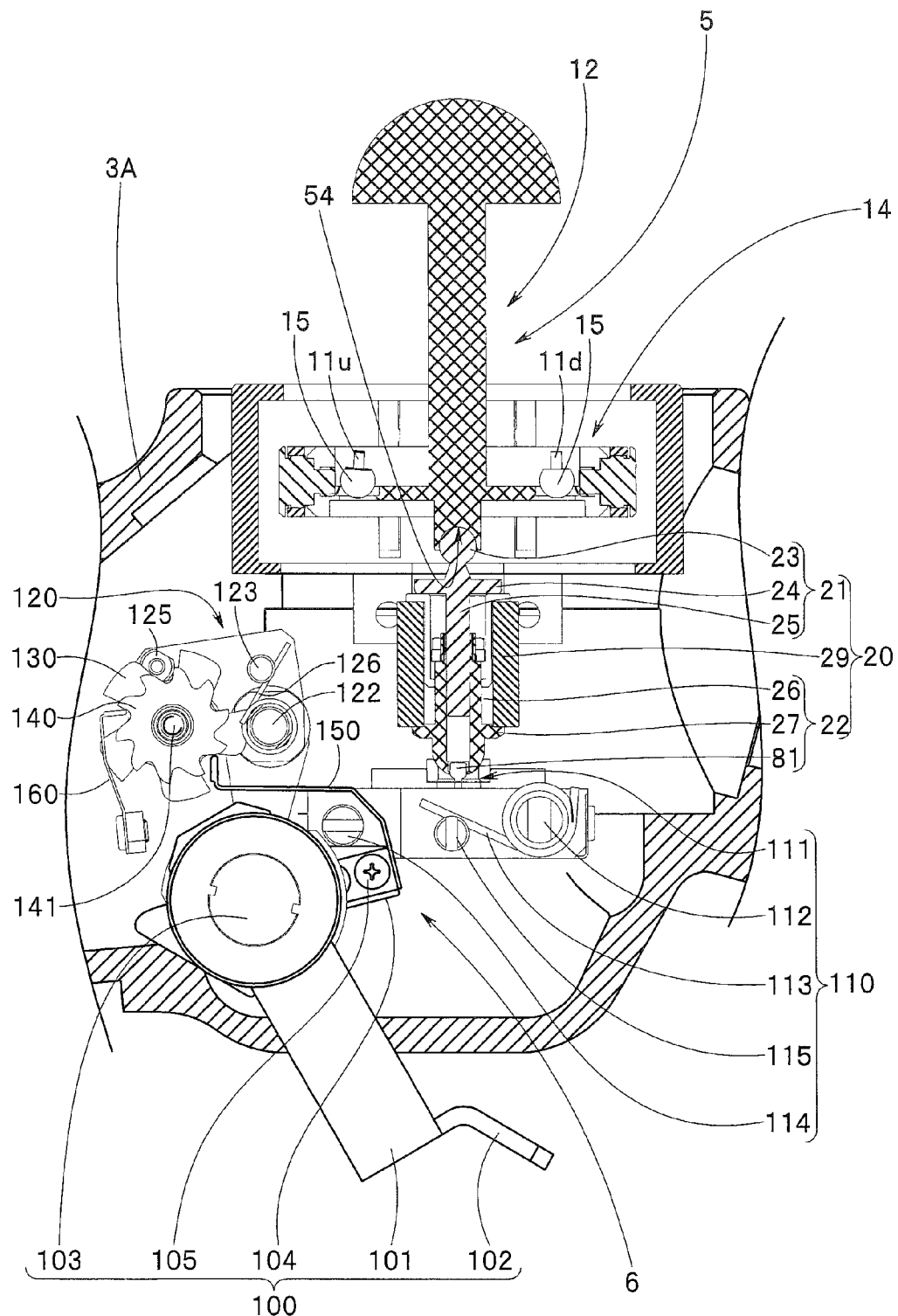
FIG. 9 is a front view in an operation portion body that forms the operation portion and is a diagram describing the semi-fixation state of the semi-fixation mechanism switch operation member.

As shown in FIG. 9, the bending operation member 5 includes the angle lever 12 and the swing frame 14, and the swing frame 14 swings along with the tilt operation of the angle lever 12. Respective proximal ends of the upper bending wire 11u and the lower bending wire 11d are fixed to the swing frame 14 by the wire locking member 15.

The operation force reduction portion connection portion 54 is provided on an end surface side of the angle lever 12 of the present embodiment. The first connection sphere portion 23 of the operation force reduction portion 20 is arranged on the operation force reduction portion connection portion 54 in a freely movable manner.

Sign 20 denotes the operation force reduction portion provided with the first reduction portion 21, the second reduction portion 22, and the spring 29. The first reduction portion 21 is provided with the first connection sphere portion 23, the first flange 24, and the slide axis 25, and the second reduction portion 22 is provided with the cylindrical portion 26, the second flange 27, and an inclination support member 81. The spring 29 that is an elastic member arranged between the first flange 24 and the second flange 27 is in a predetermined compressed state, and a support member contact portion 111 of a friction resistance member 110 is pressed against the inclination support member 81 at predetermined force to put the semi-fixation mechanism switch operation member 6 into the semi-fixation state.

The inclination support member 81 is a sphere portion forming an end portion of the second reduction portion 22. The inclination support member 81 is pivotably attached without dropping to the support member contact portion 111 of the friction resistance member 110.

Note that sign 113 denotes a first torsion coil spring, sign 114 denotes an arm member, and sign 115 denotes a spring terminal support pin. The first torsion coil spring 113 always urges the support member contact portion 111 of the friction resistance member 110 in a direction away from the second reduction portion 22.

The semi-fixation mechanism switch operation member 6 includes: the switch lever 100; the friction resistance member 110; a lever position switch arm 120; a cam 130 formed in a predetermined shape; a ratchet 140 formed in a predetermined shape; and a first leaf spring 150 and a second leaf spring 160 formed in predetermined shapes with predetermined repulsions, which are shown in FIGS. 8 to 12.

The switch lever 100 is provided with an operation plate 104 and a resistance member support pin 105 in addition to the lever body 101, the finger contact portion 102, and the lever axis 103. The operation plate 104 is integrated and fixed to the lever axis 103 and rotates about the lever axis 103 along with the operation of the switch lever 100. The resistance member support pin 105 protrudes from a back surface side of the operation plate 104, and a protruded pin portion comes in contact with and supports a bottom surface 116 of the friction resistance member 110.

Note that the resistance member support pin 105 also serves as a locking screw for fixing the first leaf spring 150 to the operation plate 104.

The lever position switch arm 120 is friction resistance member arrangement position switch means, and a switch arm body 121 is pivotably arranged around an arm axis 122. A spring terminal support pin 123 and a cam pin 125 protruding to a front surface side are provided on the switch arm body 121. Sign 124 denotes a notch portion, and the lever axis 103 can be arranged. Sign 126 denotes a second torsion coil spring that always urges the cam pin 125 provided on the switch arm body 121 in a direction pressing the cam pin 125 against a concave portion inner cam surface 131 of the cam 130.

The cam 130 and the ratchet 140 are mutually connected in an integrated manner and are pivotably arranged around a combined axis 141. The first leaf spring 150 rotates the ratchet 140 clockwise as viewed from a front surface. The second leaf spring 160 prevents the ratchet 140 from rotating counterclockwise as viewed from the front surface.

Here, working of the semi-fixation mechanism switch operation member 6 will be described.

Operation in which the user releases the semi-fixation state shown in FIGS. 9 to 12 and the like will be described.

When the user performs operation of switching the semi-fixation state to the semi-fixation release state, the user brings one of the fingers into contact with the finger contact portion 102 and moves the switch lever 100 toward an outer surface of the front cover portion 3A.

Consequently, the lever axis 103 and the operation plate 104 start rotating counterclockwise together along with the rotation of the lever body 101.

Figure 13A:
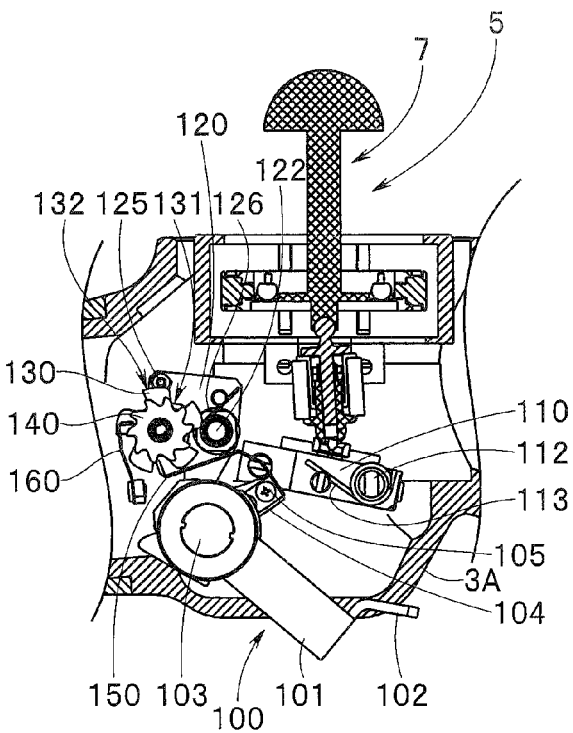
FIG. 13A is a diagram describing working of switch operation from the semi-fixation state to the semi-fixation release state.

In this case, the first leaf spring 150 fixed to the operation plate 104 rotates the ratchet 140 clockwise as shown in FIG. 13A.

The cam 130 is also rotated clockwise along with the rotation of the ratchet 140. Along with the rotation of the cam 130, the cam pin 125 is moved toward a convex portion outer cam surface 132 along a concave portion inner cam surface 131 of the cam 130 against the urging force of the second torsion coil spring 126, and the lever position switch arm 120 rotates clockwise about the arm axis 122.

Figure 13B:
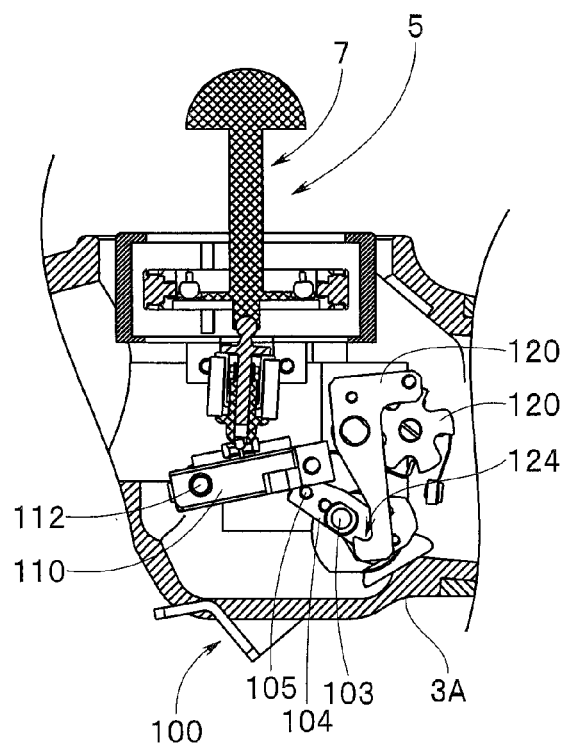
FIG. 13B is a diagram describing the working of switch operation from the semi-fixation state to the semi-fixation release state.

On the other hand, when the operation plate 104 is rotated clockwise as shown in FIG. 13B, the resistance member support pin 105 protruding to the back surface side of the operation plate 104 pushes up the friction resistance member 110, and the friction resistance member 110 is rotated counterclockwise about a resistance member axis 112.

The operation plate 104 is also rotated clockwise, and the lever position switch arm 120 is rotated counterclockwise. As a result, the lever axis 103 arranged in the notch portion 124 comes out of the notch portion 124.

The switch lever 100 is moved to a predetermined operation position near the outer surface of the front cover portion 3A. As a result, the friction resistance member 110 and the lever position switch arm 120 are rotated by predetermined amounts, and the lever axis 103 is completely out of the notch portion 124. In this case, the cam pin 125 is arranged on the convex portion outer cam surface 132 of the cam 130.

Note that during the rotation of the lever position switch arm 120, the second leaf spring 160 prevents the arm 120 from rotating in the opposite direction.

Figure 14A:
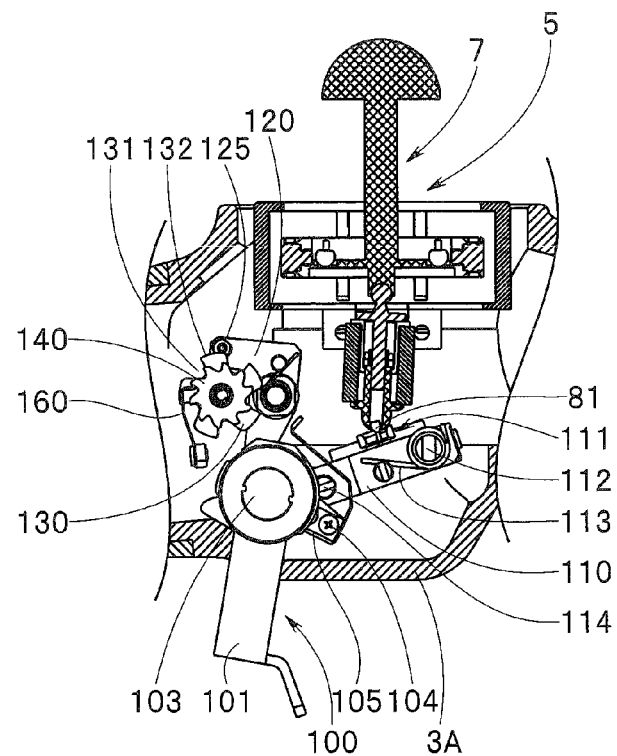
FIG. 14A is a diagram describing a state in which the semi-fixation state is switched to the semi-fixation release state.
Figure 14B:
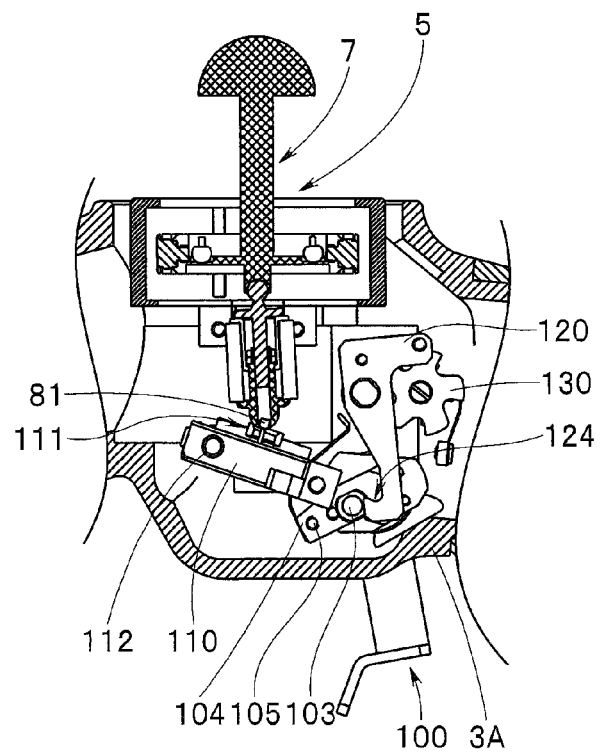
FIG. 14B is a diagram describing the state in which the semi-fixation state is switched to the semi-fixation release state.

When the operator checks that the switch lever 100 is moved to the predetermined operation position near the outer surface of the front cover portion 3A, the operator removes the finger from the finger contact portion 102. Since the lever axis 103 is completely out of the notch portion 124, the lever axis 103 does not come into contact with the lever position switch arm 120 due to the urging force of the first torsion coil spring 113, and the friction resistance member 110 rotates counterclockwise about the resistance member axis 112 as shown in FIG. 14A. As shown in FIGS. 14A and 14B, the inclination support member 81 and the support member contact portion 111 are moved by elastic force of the spring 29. The semi-fixation release state is set, in which the elastic force of the spring 29 is not applied to the support member contact portion 111 through the inclination support member 81.

As the friction resistance member 110 is rotated counterclockwise, the arm member 114 provided on the friction resistance member 110 comes into contact with the operation plate 104, and the operation plate 104 is rotated clockwise about the lever axis 103 together with the lever axis 103 as shown in FIG. 14A.

As a result, the lever body 101 integrated with the lever axis 103 is gradually separated from the outer surface of the front cover portion 3A, and the switch lever 100 reaches a semi-fixation release state position different from the semi-fixation state position as shown in FIGS. 14A and 14B.

Next, operation of switching the semi-fixation release state to the semi-fixation state will be described.

When the user performs the operation of switching to the semi-fixation state, the user brings one of the fingers into contact with the finger contact portion 102 to move the switch lever 100 toward the outer surface of the front cover portion 3A as in the operation of switching to the semi-fixation release state described above.

Consequently, the lever axis 103 and the operation plate 104 start rotating counterclockwise together along with the rotation of the lever body 101.

Figure 15A:
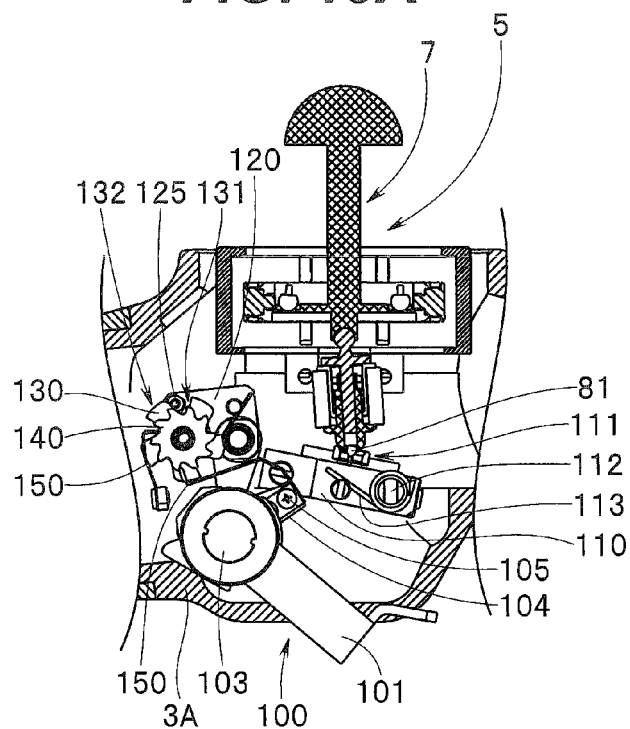
FIG. 15A is a diagram describing working of switch operation from the semi-fixation release state to the semi-fixation state.

In this case, the first leaf spring 150 fixed to the operation plate 104 rotates the ratchet 140 clockwise as shown in FIG. 15A.

The cam 130 is also rotated clockwise along with the rotation of the ratchet 140. Along with the rotation of the cam 130, the cam pin 125 is moved toward the concave portion inner cam surface 131 along the convex portion outer cam surface 132 of the cam 130 against the urging force of the second torsion coil spring 126, and the lever position switch arm 120 rotates clockwise about the arm axis 122.

Figure 15B:
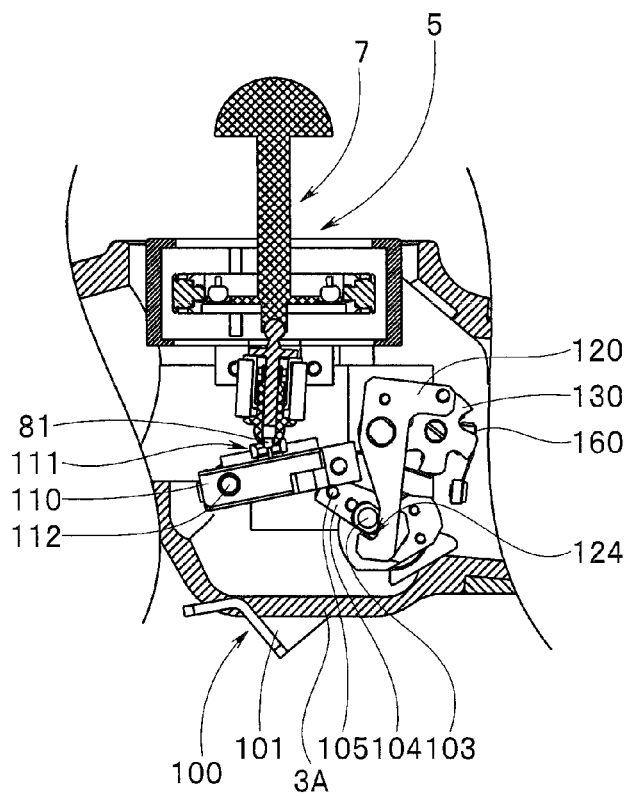
FIG. 15B is a diagram describing the working of switch operation from the semi-fixation release state to the semi-fixation state.

On the other hand, when the operation plate 104 is rotated clockwise as shown in FIG. 15B, the resistance member support pin 105 protruding to the back surface side of the operation plate 104 pushes up the friction resistance member 110, and the friction resistance member 110 is rotated counterclockwise about the resistance member axis 112.

The operation plate 104 is also rotated clockwise, and the lever position switch arm 120 is rotated counterclockwise. As a result, the lever axis 103 and the notch portion 124 are brought close to each other, and the lever axis 103 is arranged in the notch portion 124.

The switch lever 100 is moved to a predetermined operation position near the outer surface of the front cover portion 3A. As a result, the friction resistance member 110 and the lever position switch arm 120 are rotated by predetermined amounts, and the lever axis 103 is arranged in the notch portion 124. In this case, the cam pin 125 is arranged on the concave portion inner cam surface 131 of the cam 130.

Note that during the rotation of the lever position switch arm 120, the second leaf spring 160 prevents the arm 120 from rotating in the opposite direction.

Figure 10:
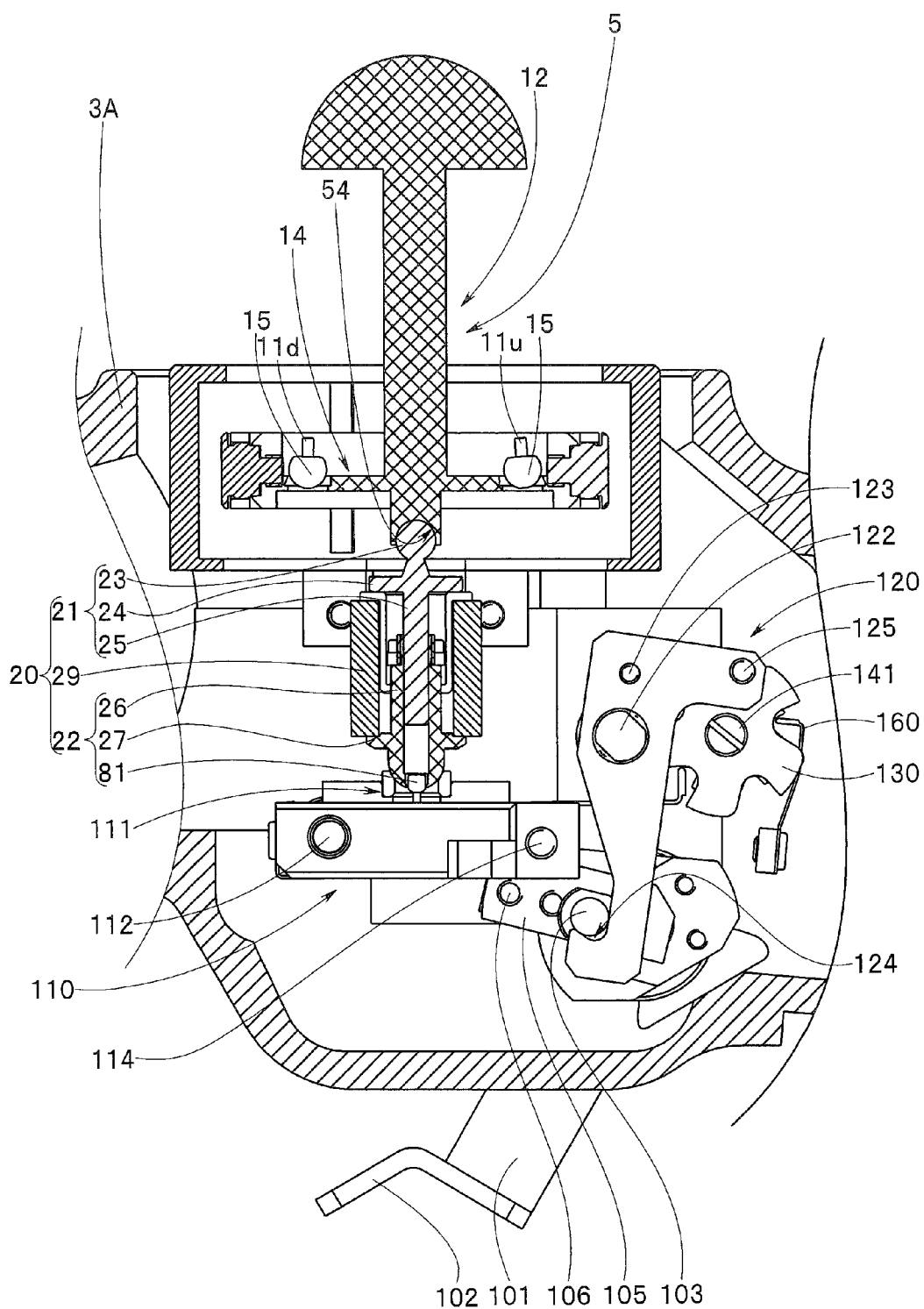
FIG. 10 is a back view in the operation portion body that forms the operation portion and is a diagram describing the semi-fixation state.
Figure 11:
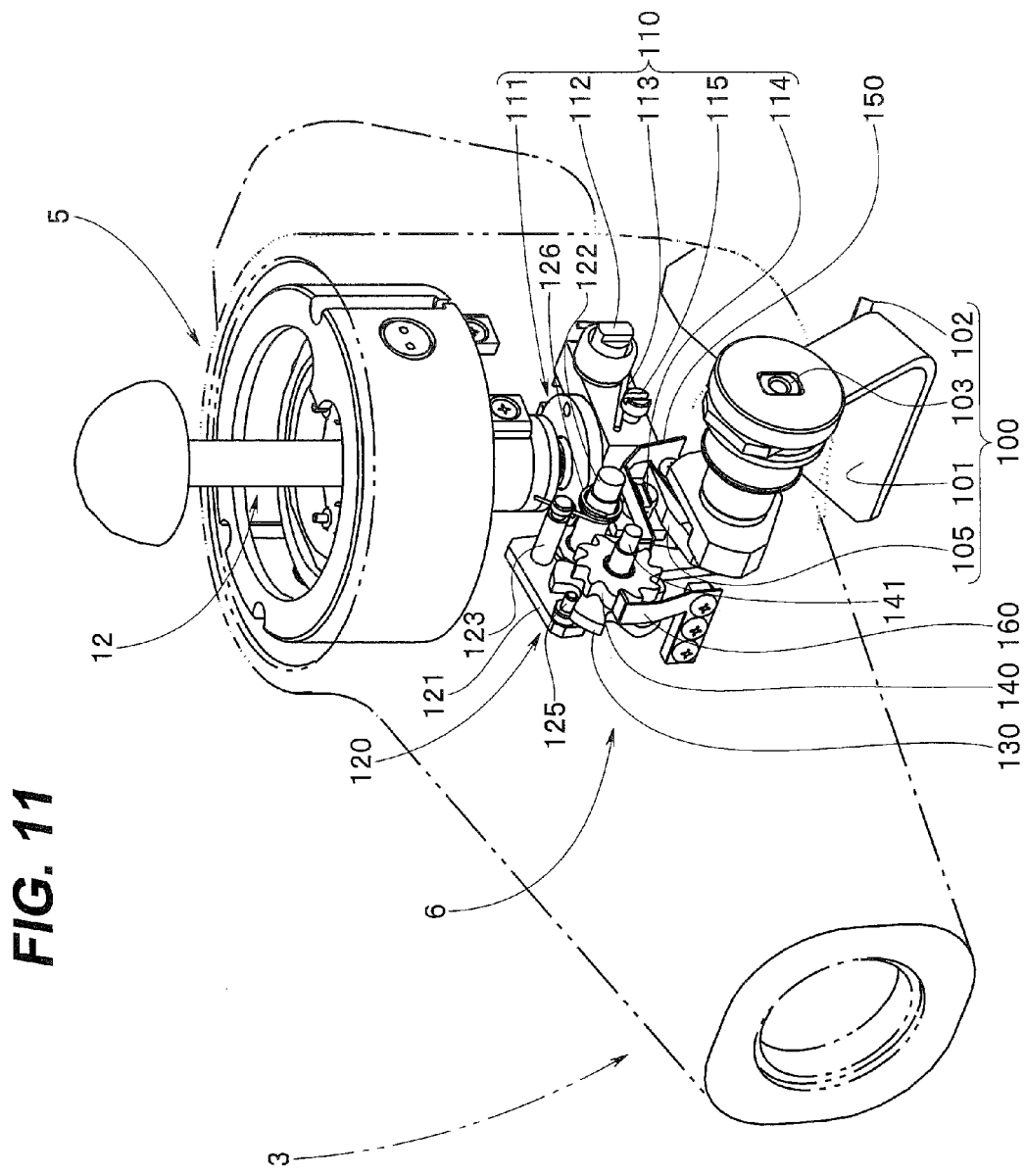
FIG. 11 is a perspective view from a front surface side of the operation portion and is a diagram describing a configuration in the operation portion body in the semi-fixation state.
Figure 12:
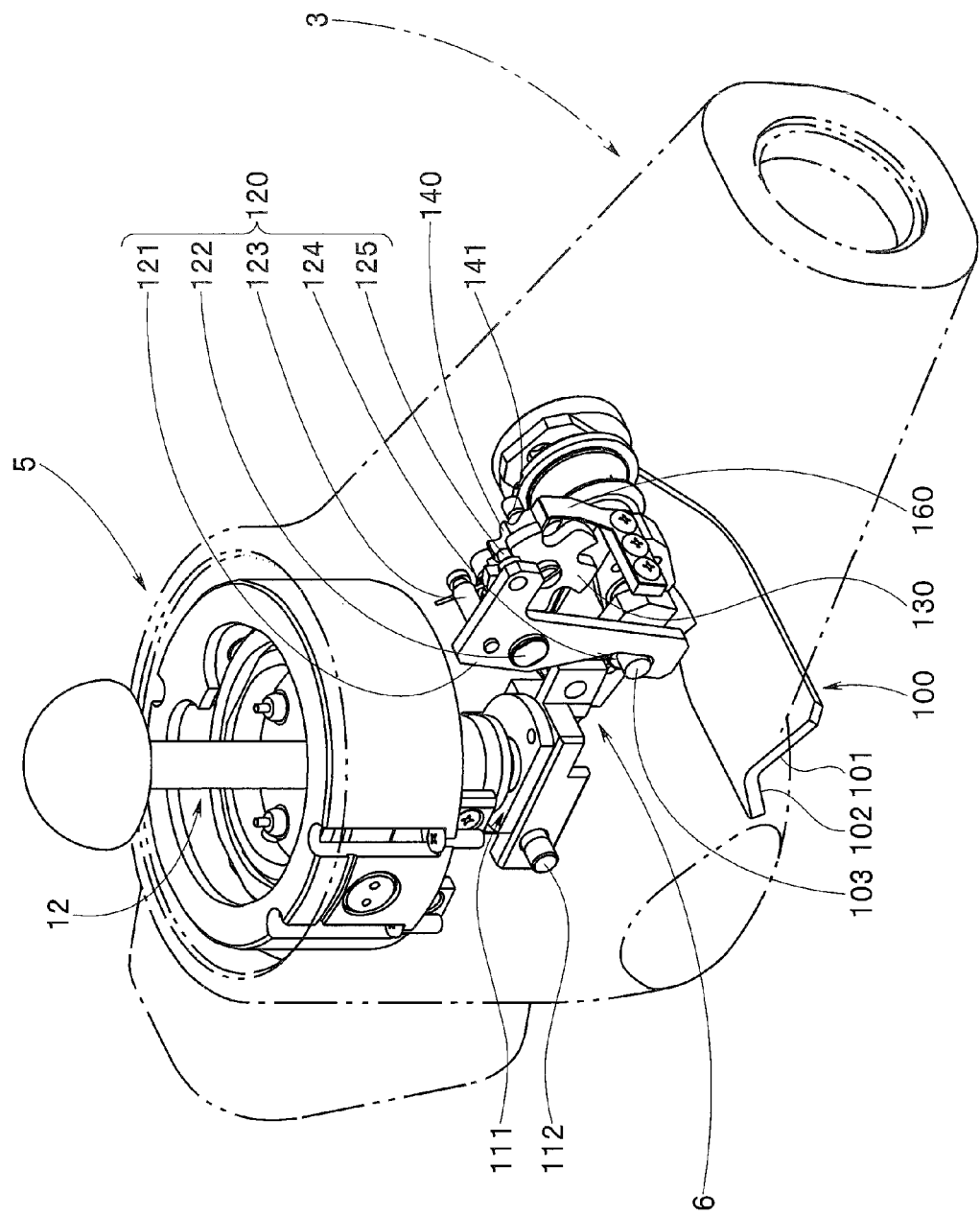
FIG. 12 is a perspective view from a back surface side of the operation portion and is a diagram describing a configuration in the operation portion body in the semi-fixation state.

When the operator checks that the switch lever 100 is moved to the predetermined operation position near the outer surface of the front cover portion 3A, the operator removes the finger from the finger contact portion 102. Since the lever axis 103 is arranged in the notch portion 124, the friction resistance member 110 is rotated counterclockwise about the resistance member axis 112 due to the urging force of the first torsion coil spring 113. As shown in FIGS. 9 and 10, the semi-fixation state is set, in which the support member contact portion 111 presses the inclination support member 81, and the spring 29 installed between the first flange 24 and the second flange 27 is in the compressed state.

As the friction resistance member 110 is rotated counterclockwise, the arm member 114 provided on the friction resistance member 110 comes into contact with the operation plate 104, and the operation plate 104 is rotated clockwise about the lever axis 103 together with the lever axis 103 as shown in FIG. 15A.

As a result, the lever body 101 integrated with the lever axis 103 is gradually separated from the outer surface of the front cover portion 3A, and the switch lever 100 reaches the semi-fixation state position different from the semi-fixation release state position as shown in FIGS. 9 and 10.

In this way, the switch lever 100, the friction resistance member 110, the lever position switch arm 120, the cam 130 formed in the predetermined shape, the ratchet 140 formed in the predetermined shape, the first leaf spring 150 formed in the predetermined shape, and the second leaf spring 160 formed in the predetermined shape are provided to form the semi-fixation mechanism switch operation member 6.

As a result, an alternate-type selector switch can be realized, in which the semi-fixation release state and the semi-fixation state can be alternately obtained by performing the rotation operation of moving the switch lever 100 toward the outer surface of the front cover portion 3A, regardless of the switch operation for operating the switch lever 100 to switch the semi-fixation mechanism switch operation member 6 from the semi-fixation state to the semi-fixation release state or the switch operation for switching the semi-fixation release state to the semi-fixation state.

The rotation-operation-type alternate-type selector switch significantly improves cleaning operability compared to a button-type alternate-type selector switch.

The lever axis 103 is arranged in the notch portion 124 in the semi-fixation state, and the lever axis 103 is arranged on a position out of the notch portion 124 in the semi-fixation release state. In this way, the arrangement position of the switch lever in the semi-fixation state and the arrangement of the switch lever in the semi-fixation release state are different positions, and whether the semi-fixation state is set can be easily determined by visually checking the arrangement position of the switch lever.

The angle lever 12 of the bending operation member 5 is provided on, for example, one surface of the front cover portion 3A included in the operation portion 3 of the endoscope 1, and the switch lever 100 of the semi-fixation mechanism switch operation member 6 is provided on the other surface of the front cover portion 3A. As a result, the operator grasping the operation portion 3 can tilt and operate the angle lever 12 by, for example, the thumb of one hand grasping the operation portion 3 and can operate the switch lever 100 by a finger other than the thumb.

Note that the present invention is not limited only to the embodiment, and various modifications can be carried out without departing from the scope of the invention.

According to the present invention, an endoscope with excellent operability can be realized, in which the bending portion can be switched to the semi-fixation state and the semi-fixation release state, and the bending operation force in bending the bending portion can be reduced.

What is claimed is:

1. An endoscope comprising:
    an insertion portion that is inserted to a portion to be observed and is provided with a bending portion bendable in at least two directions relative to an insertion axis direction;
    an operation portion continuously connected to a proximal end side of the insertion portion;
    a pulling member with a distal end connected to the bending portion, the pulling member causing the bending portion to bend by pulling;
    a bending operation member to which a proximal end of the pulling member is connected, the bending operation member being provided to be swingable about a fulcrum provided on the operation portion, the bending operation member giving pulling force to the pulling member by swinging;
    an operation force reduction portion including a first end portion and a second end portion, the first end portion being connected in a swingable manner to the bending operation member at a connection portion protruding at a predetermined height from the fulcrum, the operation force reduction portion including an elastic member that can press the bending operation member through the first end portion; and
    a switch operation member that makes a switch to a pressing state, in which the elastic member presses the bending operation member, and to a non-pressing state.

2. The endoscope according to claim 1, wherein, the first end portion and the bending operation member are connected at a position closer to the insertion portion relative to the fulcrum.

3. The endoscope according to claim 2, wherein the switch operation member is connected to the second end portion in a swingable manner.

4. The endoscope according to claim 3, wherein the switch operation member is movable forward and backward in an operation portion longitudinal axis direction and switches the pressing state and the non-pressing state by the forward and backward movement.

5. The endoscope according to claim 4, wherein the switch operation member comprises a switch lever and a slide member provided on the operation portion, and
    the slide member is arranged to be movable forward and backward in the operation portion longitudinal axis direction, and the slide member is moved forward and backward by operation of the switch lever.

6. The endoscope according to claim 1, wherein the elastic member is a coil spring.

7. The endoscope according to claim 6, wherein the bending operation member comprises a swing frame to which the proximal end of the pulling member is connected, and an angle lever that causes the swing frame to swing, the angle lever being arranged to be movable forward and backward in a lever axis direction relative to the swing frame.

8. The endoscope according to claim 7, wherein the swing frame is provided with a spherical portion that forms the fulcrum of the bending operation member, and an adjustment hole on which the angle lever is arranged such that the angle lever is movable forward and backward, and
    the angle lever is provided with an operation force reduction portion connection portion to which the first end portion of the operation force reduction portion is continuously connected in a swingable manner.

9. The endoscope according to claim 5, wherein the switch operation member is provided with a friction resistance member that holds a swing position of the bending operation member when a finger is separated from the bending operation member during bending operation.

10. The endoscope according to claim 3, wherein the switch operation member comprises:
    a lever member including a connection portion connected to the second end portion in a swingable manner, and
    a switch lever including a contact arm portion and a lever body arranged in contact with the lever member, and in a configuration in which the switch lever is pivotably connected to a first axis, and an end portion of the lever member away from the connection portion is pivotably connected to a second axis, after the switch lever is rotated and reaches a neutral state, the switch lever is switched to a pressing state or a non-pressing state by urging force of the elastic member when the switch lever exceeds an inflection point.

* * * * *